US005885248A

United States Patent [19]
Denton

[11] Patent Number: 5,885,248
[45] Date of Patent: *Mar. 23, 1999

[54] INTUBATION DETECTION SYSTEM WITH TRANSDUCER BASED INDICATOR

[75] Inventor: Marshall T. Denton, Salt Lake City, Utah

[73] Assignee: Wolf Tory Medical, Inc., Salt Lake City, Utah

[ * ] Notice: The term of this patent shall not extend beyond the expiration date of Pat. No. 5,487,731.

[21] Appl. No.: 778,612

[22] Filed: Jan. 6, 1997

Related U.S. Application Data

[63] Continuation-in-part of Ser. No. 484,936, Jun. 7, 1995, Pat. No. 5,591,130, which is a continuation-in-part of Ser. No. 199,628, Feb. 22, 1994, Pat. No. 5,487,731.

[51] Int. Cl.[6] .................................................. A61M 29/00
[52] U.S. Cl. .............................................................. 604/100
[58] Field of Search ...................... 604/100; 128/200.24, 128/200.26, 202.22, 205.23, 207.14, 207.15

[56] References Cited

U.S. PATENT DOCUMENTS

| D. 277,782 | 2/1985 | Beck . |
| D. 277,783 | 2/1985 | Beck . |
| D. 277,889 | 3/1985 | Beck . |

(List continued on next page.)

OTHER PUBLICATIONS

The capnographer discussed on pp. 2 and 3 of the specification.
The Easy Cap End–Tidal $CO_2$ detector discussed on p. 3 of the specification.
Two page instructions for the "Esophageal Intubation Detector (EID)" prepared by Wolfe Tory Medical, Inc. in 1993.
510(k) Notification from Wolfe–Carney Medical for market clearance from the Food and Drug Administration, dated Feb. 8, 1993, 32 pages.
B.A. MacLeod et al., "Verification of Endotracheal Tube Placement With Colorimetric End–Tidal $CO_2$ Detection," Annals of Emergency Medicine, 20:3 Mar. 1991, pp. 267–270 (78–81).
M.Y. K. Wee, "The Oesophageal Detector Device: Assessment of a New Method to Distinguish Oesophageal from Tracheal Intubation," Anaesthesia, 1988, 43:27–29.
K.N. Williams et al., "The Oesophageal Detector Device: A Prospective Trial of 100 Patients," Anaesthesia, 1989, 44:412–14.

(List continued on next page.)

Primary Examiner—John D. Yasko
Assistant Examiner—Manuel Mendez
Attorney, Agent, or Firm—Trask, Britt & Rossa

[57] ABSTRACT

An intubation detection system includes a pressure changing source, such as a volume changing device, connected to a transducer and an endotracheal tube. The intubation detection system determines whether the hollow tip of an endotracheal tube is in the esophagus or trachea of a patient. If the tip is in the trachea, the tip is not occluded. If the tip is in the esophagus, it becomes occluded. In one embodiment, the transducer is a pressure transducer, a chamber of a volume changing device is selectively increased in volume, and a flow restrictor is placed between the tip and the chamber and transducer. If the tip is in the trachea, when the volume is increased, the pressure at the transducer temporarily decreases, but quickly returns to atmospheric pressure. If the tip is in the esophagus, when the volume is increased, the pressure at the transducer decreases and remains at that pressure because the tip is occluded. A mass flow transducer may also be used. Analyzing circuitry receives signals from the transducer and determines the location of the tip. The analyzing circuitry control indication circuitry, which provides an indication of the location of the tip.

26 Claims, 23 Drawing Sheets

U.S. PATENT DOCUMENTS

| | | |
|---|---|---|
| 2,638,096 | 5/1953 | Waldhaus . |
| 3,991,762 | 11/1976 | Radford . |
| 4,119,101 | 10/1978 | Igich . |
| 4,346,702 | 8/1982 | Kubota . |
| 4,593,689 | 6/1986 | White . |
| 4,595,005 | 6/1986 | Jinotti . |
| 4,691,702 | 9/1987 | Chantzis . |
| 4,696,296 | 9/1987 | Palmer . |
| 4,805,611 | 2/1989 | Hodgkins . |
| 4,825,859 | 5/1989 | Lambert . |
| 4,879,999 | 11/1989 | Leiman et al. . |
| 4,938,210 | 7/1990 | Shene . |
| 4,938,741 | 7/1990 | Lambert . |
| 4,981,466 | 1/1991 | Lumbert . |
| 5,054,482 | 10/1991 | Bales . |
| 5,056,514 | 10/1991 | Dupont . |
| 5,125,893 | 6/1992 | Dryden . |
| 5,134,996 | 8/1992 | Bell . |
| 5,135,488 | 8/1992 | Foote et al. . |
| 5,163,904 | 11/1992 | Lampropoulos et al. . |
| 5,279,289 | 1/1994 | Kirk . |
| 5,287,848 | 2/1994 | Cubb et al. . |
| 5,309,902 | 5/1994 | Kee et al. . |
| 5,329,940 | 7/1994 | Adair . |
| 5,331,967 | 7/1994 | Akerson . |
| 5,339,808 | 8/1994 | Don Michael . |
| 5,360,003 | 11/1994 | Capistrano . |
| 5,368,017 | 11/1994 | Sorenson et al. . |
| 5,425,382 | 6/1995 | Golden et al. ............................ 128/899 |
| 5,513,628 | 5/1996 | Coles et al. . |

OTHER PUBLICATIONS

S.T. Sum Ping et al., "Accurancy of the FEF $CO_2$ Detector in the Assessment of Endotracheal Tube Placement," Anesth Analg, 1992;74:415–19.

W.R. Anton et al., "A Disposable End–Tidal $CO_2$ Detector to Verify Endotracheal Intubation," Annals of Emergency Medicine, 20:3 Mar. 1991, pp. 271–275 (82–86).

R.G. Foutch et al., "The Esophageal Detector Device: A Rapid and Accurate Method for Assessing Tracheal Versus Esophageal Intubation in a Porcine Model," Annals of Emergency Medicine, Sep. 1992, 21:9, pp. 1073–1076 (43–46).

J.J. O'Leary, "A Method of Detecting Oesophageal Intubation or Confirming Tracheal Intubation," Anaesth Intens Care (1988), 16, pp. 299–301.

W.A. Jenkins et al., "The Syringe Aspiration Technique to Verify Endotracheal Tube Position," from NAEMSP Abstracts, presented Jun. 19, 1992, Abstract in Prehospital and Disaster Medicine, 1992, vol. 7, Suppl. 1, 12S.

D. Oberly et al., "An Evaluation of the Esophageal Detector Device Using a Cadaver Model," Amer. J. of Emergency Medicine, vol. 10, No. 4, Jul. 1992, pp. 317–320.

P.L. Donahue, "The Oesophageal Detector Device", Anaesthesia, 1994, vol. 49, pp. 863–865.

W.A. Jenkins et al., "The Syringe Aspiration Technique to Verify Endotracheal Tube Position" American Journal of Emergency Medicine, Jul. 1994, vol. 12, No. 4, pp. 413–415.

W.P. Bozeman et al., "The Esophageal Detector Device Versus End Tidal $CO_2$ Detection in Emergency Intubations," from SAEM 1994 Annual Meeting Abstracts, 1994, 1(2) A77, #232 (Abstract in Academic Emerg Med).

K.H. Anderson et al., Forum "Assessing the position of the tracheal tube. The reliability of different methods." Anaesthesia, 1989, vol. 44, pp. 984–985.

Linda Zaleski et al., "The Esophageal Detector Device, Does It Work?", Anesthesiology, 1993, 79:244–47.

M.R. Salem et al., "Efficacy of the Self–inflating Bulb in Detecting Esophageal Intubation, Does the Presence of a Nasogastric Tube or Cuff Deflation Make a Difference?", Anesthesiology, Jan. 1994, 80:42–48.

N.S. Morton et al., "The Oesophageal Detector Device: Successful Use in Children," Correspondence, Anaesthesia, 1989, 44:523–24.

A. Baraka et al., "The Esophageal Detector Device in the Morbidlty Obese," Letters to the Editor, Anesth Analg, 1993, 77(2):400.

M.K.Y. Wee, "Comments on the Oesophageal Detector Device," Correspondence, Anaesthesia, 1989, 44:930–31.

A. Baraka, "The Oesophageal Detector device in the asthmatic patient," Correspondence, Anaesthesia, 1993, 48(3):275.

S.R. Haynes et al., "Use of the oesophageal detector device in children under one year of age," Anaesthesia, 1990, vol. 45, pp. 1067–1069.

Y.L. Burnett et al., "Efficacy of the Self–inflating bulb in verifying tracheal tube placement in children." Abstract in Anesth Analg 1995;80;S63.

P.K. Sood et al., The Esophageal detector device: Ellick's evacuator versus syringe [letter]. Anesthesiology 1995;82:314.

Y. Wafai, et al. "The self–inflating bulb in detecting esophageal intubation: Effect of bulb size and technique used." Abstracts in Anesthesiology 1993;79(3A):A496.

Y. Wafai et al., "The self–inflating bulb for confirmation of tracheal intubation: Icidence and demography of false negatives." Abstract in Anesthesiology 1994;81(3A):A1304.

M.R. Salem et al., Comments on the self–inflating bulb [letter]. Anesthesiology 1995;82:315–316.

Y. Wafai et al., "Effectiveness of the self–inflating bulb for verification of proper placement of the esophageal tracheal combitube." Anesth Analg 1995;80:122–126.

W.H. Petroianu et al., Detection of an oesophageal intubation: State of the art [letter]. Anaesth Intensive Care 1994;22(6):744–746.

P. Clyburn et al., Accidental oesophageal intubation. Br J Anaesth 1994; 73:55–63.

CD Marley et al.: Evaluation of a prototype esophageal detection device. Acad Emerg Med 1995;2:503–507.

P.G. Schafer et al., "Use of the Esophageal Intubation Detector–Whistle for Detecting Esophageal of Tracheal Intubator", Anesthesiology, Sep. 1995, vol. 83, No. 3A.

P.G. Schafer et al., "The Electronic Esophageal Detector Device for Detection of Tracheal and Esophageal Intubation: Does it Work?", Anesthesiology, Sep. 1996, vol. 85, No. 3A.

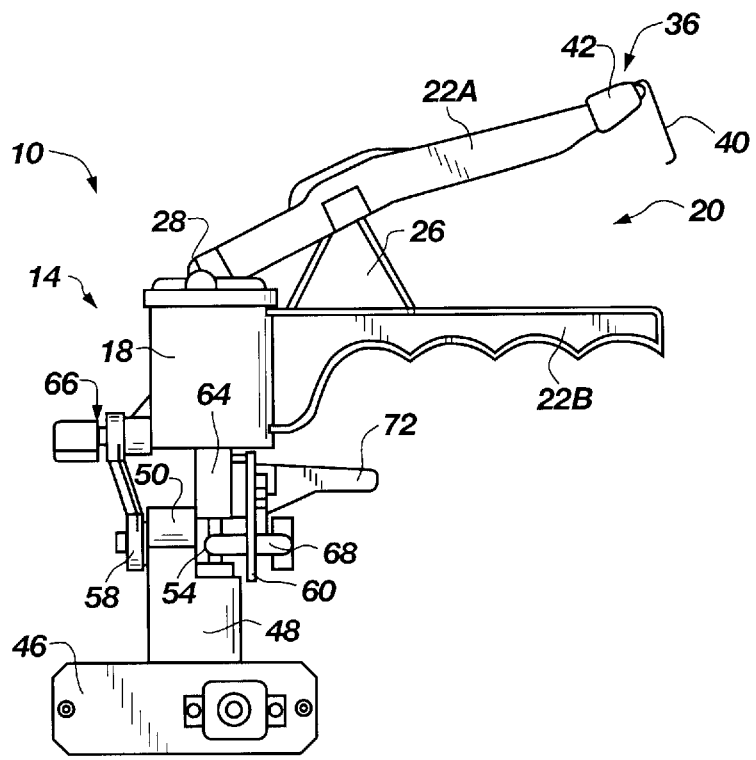
Fig. 1A
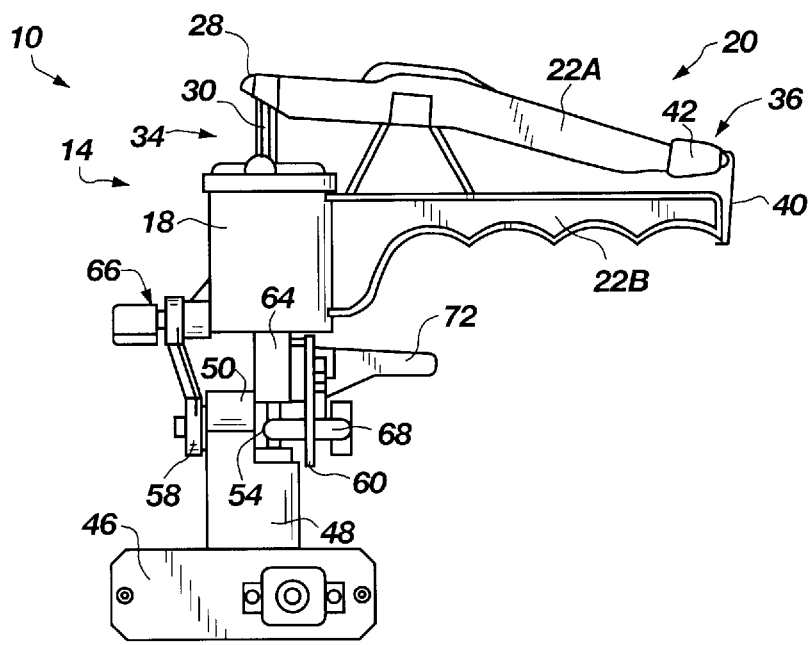
Fig 1.B

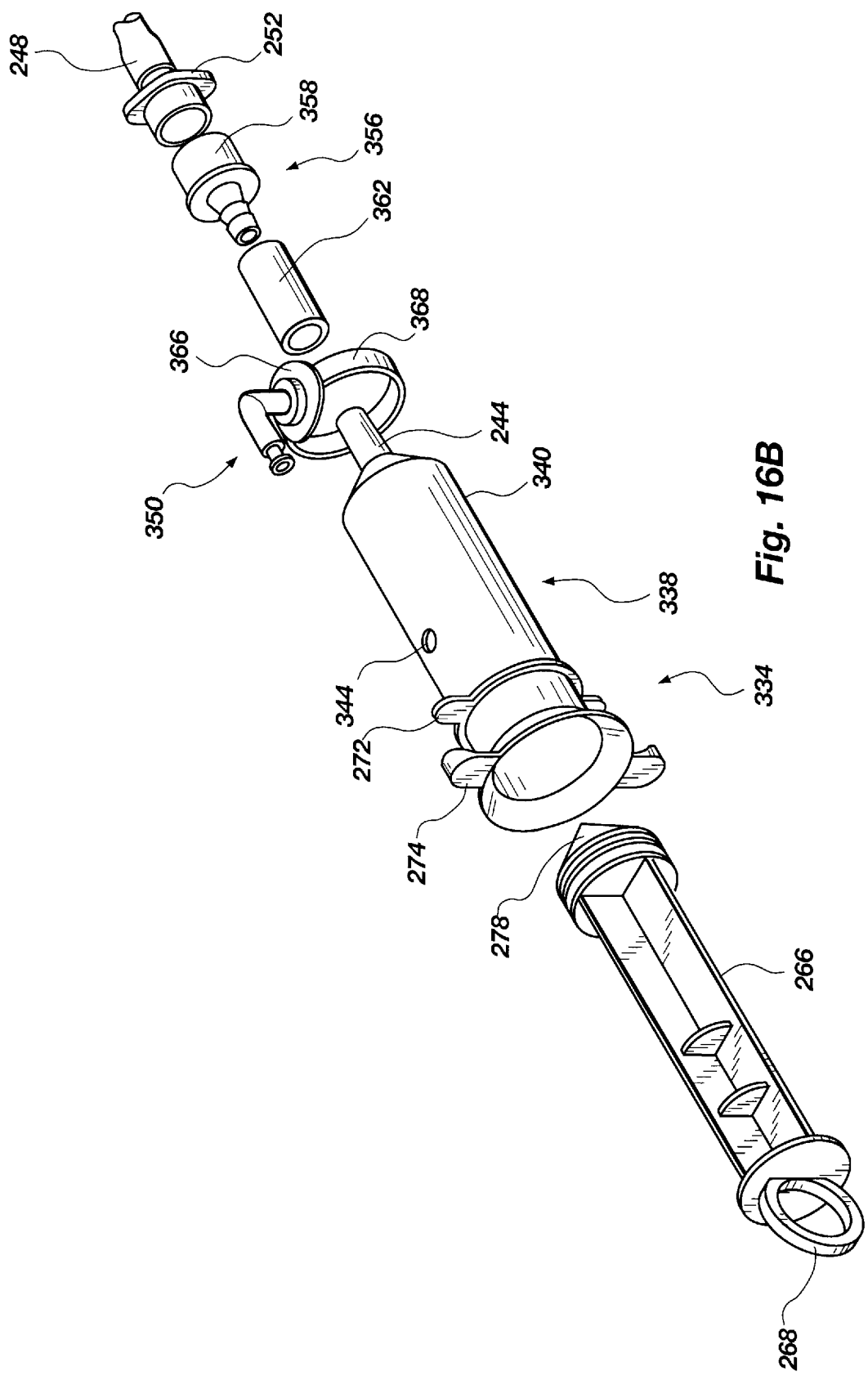

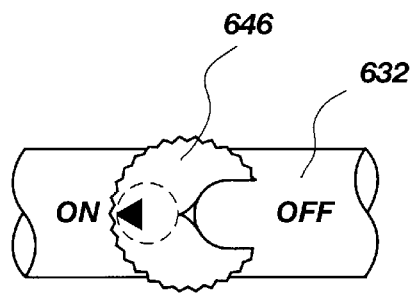
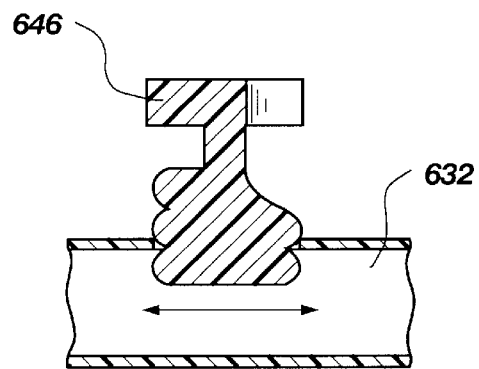
*Fig. 29A*  *Fig. 29B*
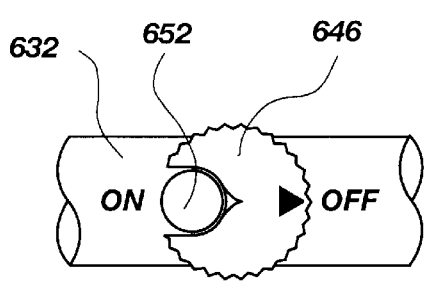
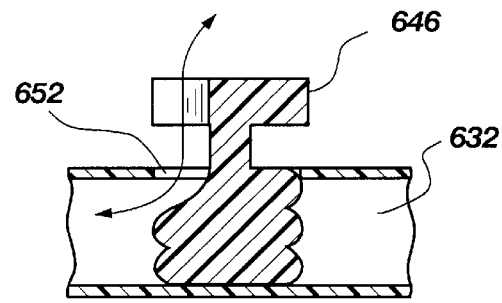
*Fig. 30A*  *Fig. 30B*

INTUBATION DETECTION SYSTEM WITH TRANSDUCER BASED INDICATOR

RELATED APPLICATIONS

This application is a continuation-in-part of application Ser. No. 08/484,936, filed Jun. 7, 1995, now U.S. Pat. No. 5,591,130, which is a continuation-in-part of application Ser. No. 08/199,628, filed Feb. 22, 1994, now U.S. Pat. No. 5,487,731.

BACKGROUND OF THE INVENTION

1. Field of the Invention

The present invention relates to an intubation detection system, more particularly, to a transducer based intubation detection system with an indicator that indicates whether an endotracheal tube (or other tubular airway controlling device) is in a patient's esophagus or in the patient's trachea, immediately following an attempted intubation.

2. State of the Art

Endotracheal tubes may be used to pump oxygen enriched air into the lungs of a patient. The procedure is used in the operating room, the emergency department, and prehospital care settings, such as accident sites. One end of the endotracheal tube is connected to a source of oxygen and the other end is placed in the patient's trachea, in a procedure referred to as intubation. A danger in intubation is that the endotracheal tube may be placed in the esophagus rather than the trachea. Even an experienced clinician has difficulty in properly placing the endotracheal tube. Improper placement of the tube may result in permanent injury or death. Accordingly, detection of improper placement of the endotracheal tube is extremely important.

Clinical examination alone is dependent on the clinician's experience and judgement and may give misleading results. For this reason, accessory devices exist that help determine if the trachea is properly intubated. For example, capnographers have been used to detect improper placement. A capnographer is an expensive instrument that detects the presence of $CO_2$. Confirmation of proper endotracheal tube placement is based on the fact that carbon dioxide is present in exhaled air in approximately 5% concentration, but is present in esophageal gas in only minute concentrations. The capnographer is a relatively large, sophisticated, and expensive reusable instrument that has a valid use in hospital operating rooms. The capnographer is too bulky, too expensive, and requires too much time to calibrate for routine use in prehospital settings and emergency departments. Unfortunately, it is these settings where experience may be limited and where esophageal intubations more frequently occur.

The EASY CAP End-Tidal $CO_2$ detector is a currently available disposable device for use outside the operating room that assists in distinguishing esophageal from tracheal intubations by a color indication. The EASY CAP End-Tidal $CO_2$ detector is marketed by Nellcor Inc. (formerly produced and distributed by FENEM Airway Management Systems under the name "FEF End-Tidal $CO_2$ detector"). After intubation is performed, the $CO_2$ detector device is attached to the endotracheal tube in line with the oxygen bag. Oxygen is insufflated through the device into the endotracheal tube and lungs, then exhaled back through the device. A change of color from purple to yellow with each breath indicates tracheal intubation. If the endotracheal tube is in the esophagus, no $CO_2$ is detected and the color change does not occur.

The $CO_2$ detector device will not easily detect tracheal intubation in the patient who is pulseless or inadequately perfusing the pulmonary circulation. This is due to inadequate $CO_2$ exhalation. It will still detect esophageal intubation in these patients. However, many tracheal intubations will be interpreted as esophageal due to lack of color change. Clinical judgement is required in these cases.

Another technique for distinguishing esophageal from tracheal intubation is described in M. Y. K. Wee, "The oesophageal detector device assessment of a new method to distinguish oesophageal from tracheal intubation," Anaesthesia, 43:27–29 (1988). This technique relies on the relative rigidity of the tracheal wall, as compared to that of the esophagus. The trachea remains constantly patent due to C-shaped rings of cartilage supporting its lumen. The esophagus will collapse over the end of a rigid tube when significant negative pressure (with respect to atmospheric pressure) is applied in the tube, thus preventing aspiration of air. The more rigid trachea, on the other hand, remains open and allows free aspiration of air, when significant negative pressure is applied in the tube.

Under the technique, a detector device includes a syringe that is attached to an adaptor. After intubation, the adaptor is connected to the endotracheal tube. Air is aspirated into the syringe by pulling the syringe plunger. Free flow of air (i.e., ease in pulling the syringe plunger) is indicative of proper tube placement in the trachea. Resistance to flow (i.e., resistance to pulling the syringe plunger) indicates that the endotracheal tube may be improperly placed.

SUMMARY OF THE INVENTION

An intubation detection system includes a pressure changing source that may provide a change in pressure to a chamber and to a tube connected to the chamber. In one embodiment, a transducer provides an electrical signal indicative of pressure at the transducer, which may be the same as at the chamber. The tube includes an endotracheal tube or is connected to an endotracheal tube or other tubular airway controlling device. The pressure at the transducer may be influenced by whether the tip of the endotracheal tube is occluded. If the tip is in the trachea, the tip is not occluded. If the pressure at the transducer is less than the pressure in the trachea, the pressure at the transducer will increase. If the tip is in the esophagus, the pressure at the transducer will remain very constant.

A flow restrictor may be positioned between the endotracheal tube tip and the chamber and transducer. A flow restrictor facilitates initial negative pressure at the transducer.

The pressure changing source may be an automatically or manually operated volume changing device. When the volume decreases, the pressure tends to decrease. A bulb and/or gas canister may be used.

Analyzing circuitry determines whether the tube is in the esophagus or trachea. The analyzing circuitry may also detect the prepense of certain potential problems. Indication circuitry may provide an indication of the position of the tip as well as other information.

A mass flow transducer may also be used in place of or in addition to a pressure transducer.

An O-ring may be used between adapters to increase the seal between the adapters or to create a seal where there otherwise would not be a seal.

There are various other embodiments of the invention in which an intubation detector system including an indicator provides an indication of whether a tubular airway controlling device, such as an endotracheal tube, is in a patient's esophagus or trachea. In one embodiment of the invention, an esophageal intubation detector includes a syringe that is connected to the endotracheal tube through an adapter.

The adapter includes an orifice over which an indicator is positioned. The indicators may be activated in response to a significant pressure differential across the indicator. A variety of indicators, including audible, visual, and transducer indicators, may be used. The indicators may provide an audible, visual, tactile, and/or electrical signal indicating the position of the endotracheal tube. Some indicators may only provide signals indicating the endotracheal tube is in the esophagus. The clinician infers that the endotracheal tube is in the trachea from the absence of the signal. Other indicators may provide signal(s) that positively indicate that the endotracheal tube is in the trachea, and/or the signal(s) from the indicator may be processed to positively indicate that the endotracheal tube is in the trachea.

The present invention is not limited to using a syringe, but may include other sources of negative pressure. For example, a bulb may be a volume changing device. The bulb may be used in connection with a resuscitator bag. Following being squeezed, the bulb increases volume by returning to its natural shape.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

FIG. 1A is a side view of an intubation detection system according to one embodiment of the present invention in which a movable lever is in a raised position.

FIG. 1B is a side view of the intubation detection system of FIG. 1A in which the movable lever is in a lowered position.

FIG. 16B is an exploded view of the esophageal intubation detector of FIG. 16A and a portion of the endotracheal tube.

FIG. 29A shows a top view of a vent switch of the intubation detector/resuscitator system of FIGS. 28A and 28B in the ON position.

FIG. 29B shows a side view of the vent switch of FIG. 29A in the ON position.

FIG. 30A shows a top view of the vent switch of FIG. 29A in the OFF position.

FIG. 30B shows a side view of the vent switch of FIG. 29A in the OFF position.

DETAILED DESCRIPTION OF PREFERRED EMBODIMENTS

A. Transducer-Based Systems

Figure 2:
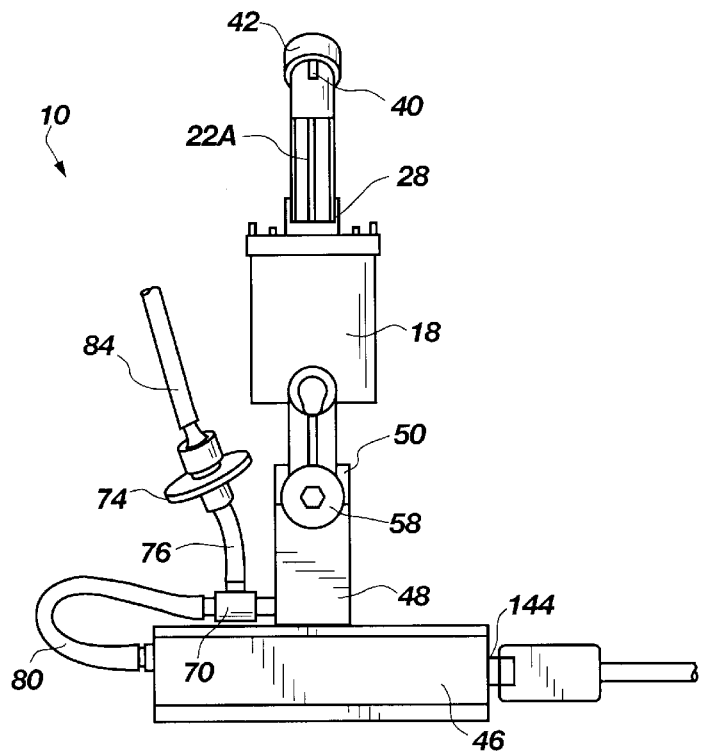
FIG. 2 is a front view of the intubation detection system of FIG. 1.

FIGS. 1A and 1B illustrate side views and FIG. 2 illustrates a front view of an intubation detector system 10. The embodiment illustrated in FIGS. 1A, 1B, and 2 is a prototype. An actual commercial embodiment may differ somewhat functionally, as described below, as well as differing cosmetically. Further, the particular mechanical structure chosen for the prototype is not required in other embodiments of the invention.

Intubation detection system 10 includes volume changing device 14, which is an example of a pressure changing source. Volume changing device 14 includes a chamber 120 (shown in FIG. 5) inside a cylindrical casing 18. Volume changing device 14 also includes volume changing actuator 20, which in the embodiment of FIGS. 1A and 1B includes a movable lever 22A and a stationary grip 22B. Movable lever 22A pivots about a fulcrum 26. An end 28 of lever 22A is connected to a shaft 30 of a plunger 34. In FIG. 1A, shaft 30 is completely inside casing 18. In FIG. 1B, lever 22A has been squeezed toward grip 22B. As shown in FIG. 1B, as lever 22A pivots about fulcrum 26, an end 36 of lever 22A moves toward grip 22B, while end 28 pulls shaft 30 upward from casing 18.

A clip 40 is connected to end 36 of lever 22A. In FIGS. 1A and 1B, clip 40 is shown being connected through a strong silicon band 42. In a commercial embodiment, however, if clip 40 is used, it may be connected in various other ways. Clip 40 holds lever 22A stationary after lever 22A is squeezed by a clinician toward grip 22B. While lever 22A is stationary, the size of the chamber in casing 18 is constant. Therefore, while lever 22A is stationary, if there are changes in pressure inside intubation detection system 10, the changes are due to factors other than the volume of chamber 120, such as air passing through the tip of an endotracheal tube, as described below. If lever 22A is allowed to move (e.g. completely or partially back to the position shown in FIG. 1A) during a test, it might cause a change in pressure at the transducer 130 (shown in FIG. 5).

Referring to FIGS. 1A, 1B, and 2, intubation detection system 10 includes an electronics chassis 46 that supports a block 48, which in turn supports volume changing device 14. A commercial embodiment may look somewhat sleeker. The particular volume changing device 14 illustrated in FIGS. 1A, 1B, and 2 is marketed under the mark Mityvac, by Neward Enterprises, Cucamonga, Calif. (Of course, various other pressure changing sources could be used. A pressure changing source could be automated as opposed to manual. An automated pressure changing source could be actuated in response to the clinician pushing a button, rather than squeezing levers 22A and 22B.) A block 50 helps hold volume changing device 14 in place. Volume changing device 14 includes a horizontal, generally cylindrically shaped section 54 that extends between a covering 58 and a vertical support 60. Section 54 extends between blocks 48 and 50. A channel 126 (shown in FIG. 5), which may be a tube, extends from chamber 120 in casing 18 through a vertical cylindrical section 64, section 54, and block 48, to a three-way connector 70. (Again, the particular structural details of the system of FIGS. 1A, 1B, and 2 are not required.)

Referring to FIG. 2, a flow restrictor 74 is connected to three-way connector 70 through a short tube 76. Transducer 130 (shown in FIG. 5) is positioned in chassis 46 and is connected to three-way connector 70 through a tube 80. In a commercial embodiment, tube 80 would preferably extend directly downward from three-way connector 70 to the transducer in chassis 46. Alternatively, the three-way connector could be inside block 48.

Figure 3:
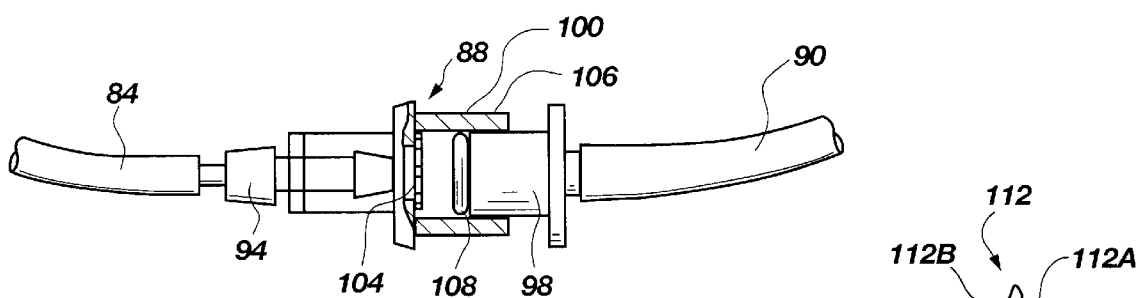
FIG. 3 is a side view of adapters joining two tubes used in connection with the system of FIG. 1.
Figure 4:
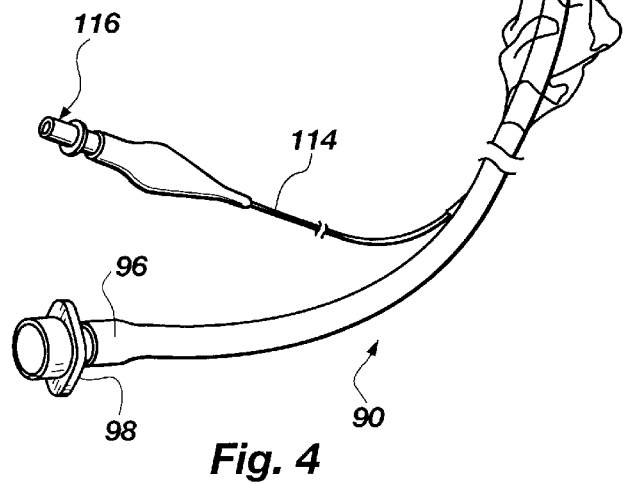
FIG. 4 is a perspective view of an endotracheal tube used in connection with the system of FIG. 1.

Referring to FIGS. 2, 3, and 4 (shown in different scales), a tube 84 is connected to flow restrictor 74 and to an adapter 88. Adapter 88 connects tube 84 to an endotracheal tube 90. Adapter 88 may be connected to tube 84 through a luer lock adapter 94. That is, adapter 88 includes a well known element that rotates into and locks with luer lock adapter 94. An end 96 of endotracheal tube 90 is connected to an adapter 98 (which may be considered part of endotracheal tube 90). Adapter 88 includes a female connector port 100 into which adapter 98 may be selectively inserted and removed. A biofilter 104 is positioned in adapter 88 to prevent infection in endotracheal tube 90 from passing to reuseable structure, described below. Biofilter 104 may be of a well known variety.

Adapters 88 and 98 should be selected so that there is a seal between female connector port 100 and adapter 98 that prevents air from leaking. However, as a secondary backup precaution, an O-ring 108 may also be used. Prior to use, O-ring 108 may be (but is not required to be) positioned near the outer edge 106 of female connector port 100. As adapter 98 is inserted into female connector port 100, O-ring 108 asserts a back pressure onto adapter 98. If there is otherwise no seal between adapter 98 and female connector port 100, the back pressure may create a seal. If there is otherwise a seal, the back pressure may increase the strength of the seal.

Endotracheal tube 90, adapter 98, and adapter 88 may be disposable, and are referred to as disposable structure. By contrast, volume changing device 14, chassis 46 and associated electronic circuitry, three-way connector 70, tube 76, flow restrictor 74, tube 84 and luer lock adapter 94 may be reusable, and are referred to as reusable structure. Alternatively, the dividing line between disposable and reusable structure could be somewhere else. Whether to consider the disposable structure part of intubation detection system 10 is arbitrary. Indeed, the reusable structure may be sold separately from the disposable structure and vice versa.

One version of endotracheal tube 90 includes an inflatable balloon 110 and a tip 112, which may include holes 112A and 112B. Balloon 110 may be inflated through a tube 114 and connection port 116. Of course, the details of endotracheal tube 90 could be different without departing from the present invention.

Figure 5:
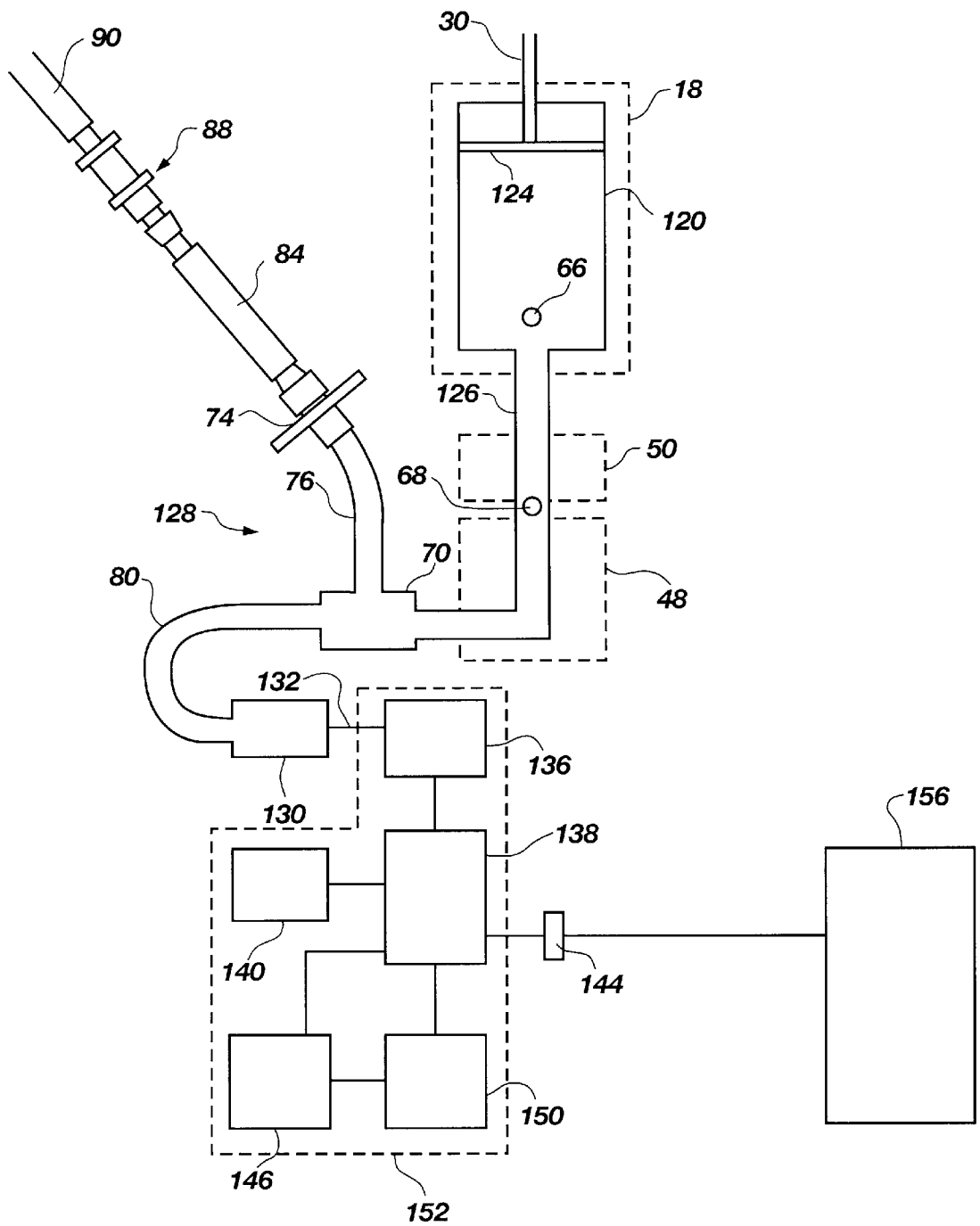
FIG. 5 is a partially schematical and partially block diagram representation of the system of FIG. 1.

FIG. 5 illustrates electrical circuitry 152 (shown in dashed lines) of intubation detection system 10 that interfaces with mechanical structure of intubation detection system 10. A chamber 120 is inside cylindrical casing 18 (shown in dashed lines). A plunger seal 124 is connected to and moves up and down with shaft 30. A channel 126 connects chamber 120 to three-way connector 70. The general position of blocks 50 and 48 are shown in dashed lines. Channel 126, three-way connector 70, tube 76, and tube 80 form an antechamber 128 that has the same or very close to the same air pressure as in chamber 120. As used herein, the term "air" is intended to be inclusive of various gases and not to be narrowly construed.

Transducer 130 (or other sensing structure) provides an electrical representation of the air pressure in tube 80 through an electrical signal(s) on a conductor(s) 132. Signal conditioning circuitry 136 receives the electrical signal and provides a conditioned version of it to analyzing circuitry 138. Signal conditioning circuitry 136 may be as simple as an analog to digital converter or may also include some filtering. Analyzing circuitry 138 may be a microprocessor or dedicated hardware (e.g. including gate arrays). Optional memory 140 may include ROM and/or RAM for analyzing circuitry 138. A power source 146 may be an AC, DC, battery, or other power source.

Figure 6:
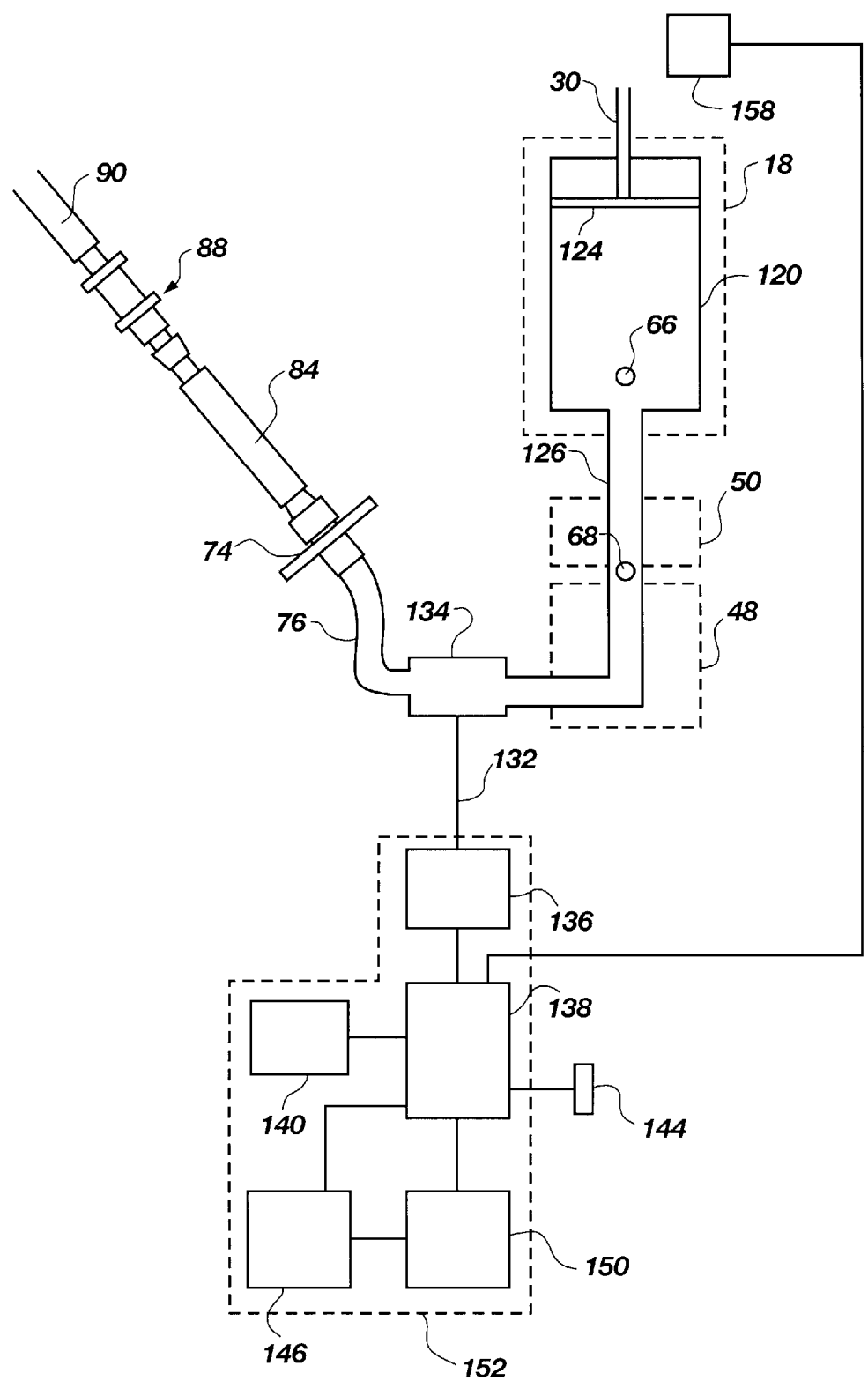
FIG. 6 is a partially schematical and partially block diagram representation of an alternative intubation detection system according to the present invention.

As shown in FIG. 5, transducer 130 is a pressure transducer. Various well known pressure transducers (e.g. with a Whetstone bridge) may be used. Alternatively, as shown in FIG. 6, a transducer 134 is a mass flow transducer that provides an electrical signal(s) to signal conditioning circuitry 136 indicative of flow of air through transducer 134. In a preferred embodiment, air flows when tip 112 is in the trachea. With other arrangements, air could flow under different conditions. Various transducers and experience in constructing transducer based systems are available through Industrial Data Systems, Salt Lake City, Utah. In FIG. 6, transducer 134 is connected between channel 126 and tube 76, so that three-way connector 70 is not used.

Figure 7:
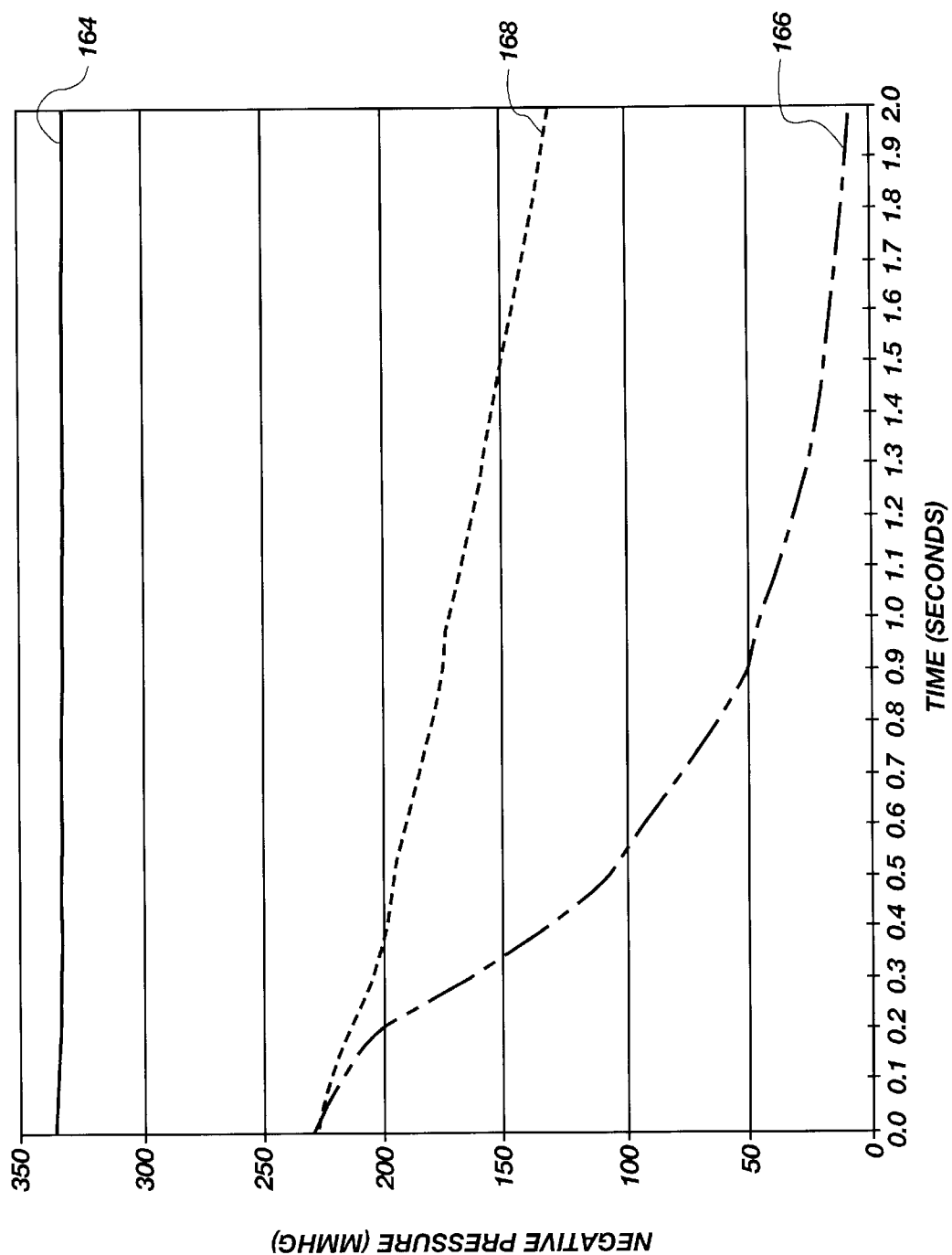
FIG. 7 is a graphical representation of negative pressure vs. time curves of three intubations.

Analyzing circuitry 138 detects changes in pressure at transducer 130, changes in mass flow through transducer 134, or some other phenomenon at other sensing structure, over time. Merely as an example, FIG. 7 is a graph of (negative) pressure vs. time for the pressure at transducer 130 for three different intubations with the system of FIG. 1. The graph of FIG. 7 is merely intended to show general possibilities. Actual pressure vs. time curves for particular embodiments of the invention may differ somewhat from that of FIG. 6. Curve 164 represents the case in which tip 112 of endotracheal tube 90 is inserted into the esophagus of the patient. When lever 22A is lowered, plunger seal 124 is raised which increases the volume of chamber 120 and the volume of the combined chamber 120 and antechamber 128 so that the pressure in chamber 120 and antechamber 128 tends to decrease.

An optional RS-232 port 144 or other port may be used to communicate with the outside world, such as optional computer, printer, and/or memory 156. Port 144 is optional in the following sense. In ordinary operation in the field, there may be no reason for analyzing circuitry 138 to have the ability to communicate with electronic devices outside of intubation detection system 10 shown in FIG. 1. Alternatively, even in field operation, there may be value in connecting a portable intubation detection system to a more powerful computer that may include a display and/or a printer for more detailed analysis. Alternatively, with appropriate analyzing circuitry 138, RS-232 port 144 could be connected directly to a printer.

Flow restrictor 74 contributes to the rate at which pressure decreases. Negative pressure is below atmospheric pressure. An increase in negative pressure is a decrease in pressure and a decrease in negative pressure is an increase in pressure. Intubation detection system 10 could be constructed to begin at other than atmospheric pressure. Flow restrictor 74 may be any of various device including a well known disc filter. The filter material in the disc filter restricts air flow.

Without flow restrictor 74 or another device performing the same function, if tip 112 were in the trachea, the pressure at transducer 130 would stay at near atmospheric pressure. However, with flow restrictor 74, negative pressure builds quickly in antechamber 128, and somewhat less quickly in endotracheal tube 90.

Referring to FIG. 7, when tip 112 is in the esophagus, as is the case of curve 164, the walls of the esophagus occlude holes 112A and 112B of tip 112 which allows the negative pressure at transducer 130 to continue to increase to about 335 MMHG. Because holes 112A and 112B of tip 112 are occluded, the negative pressure remains very constant for the two seconds shown in FIG. 7.

In the case of curve 166, tip 112 is in the trachea and does not become occluded. However, flow restrictor 74 allows the negative pressure at transducer 130 to increase to about 230 MMHG. However, air is allowed to pass through holes 112A and 112B, endotracheal tube 90, and flow restrictor 74 to antechamber 128, and thereby decrease the negative pressure at transducer 130. Because of flow restrictor 74, the air from holes 112A and 112B does not instantly decrease the negative pressure at transducer 130. However, the decrease in negative pressure is fairly abrupt, as shown in FIG. 7.

In the case of curve 168, tip 112 of endotracheal tube 90 may be in the trachea. However, the decrease in negative pressure is not as great as in the case of curve 166. A curve such as curve 168 may be created by a patient with endotracheal tube obstruction, morbid obesity, pulmonary edema, mainstem bronchus intubation, severe bronchospastic, or obstructive lung disease. At any rate, a curve such as curve 168 is an indicator that something may be wrong with the patient. At a minimum, it is cause to take extra care and/or do additional tests where possible.

Figure 8A:
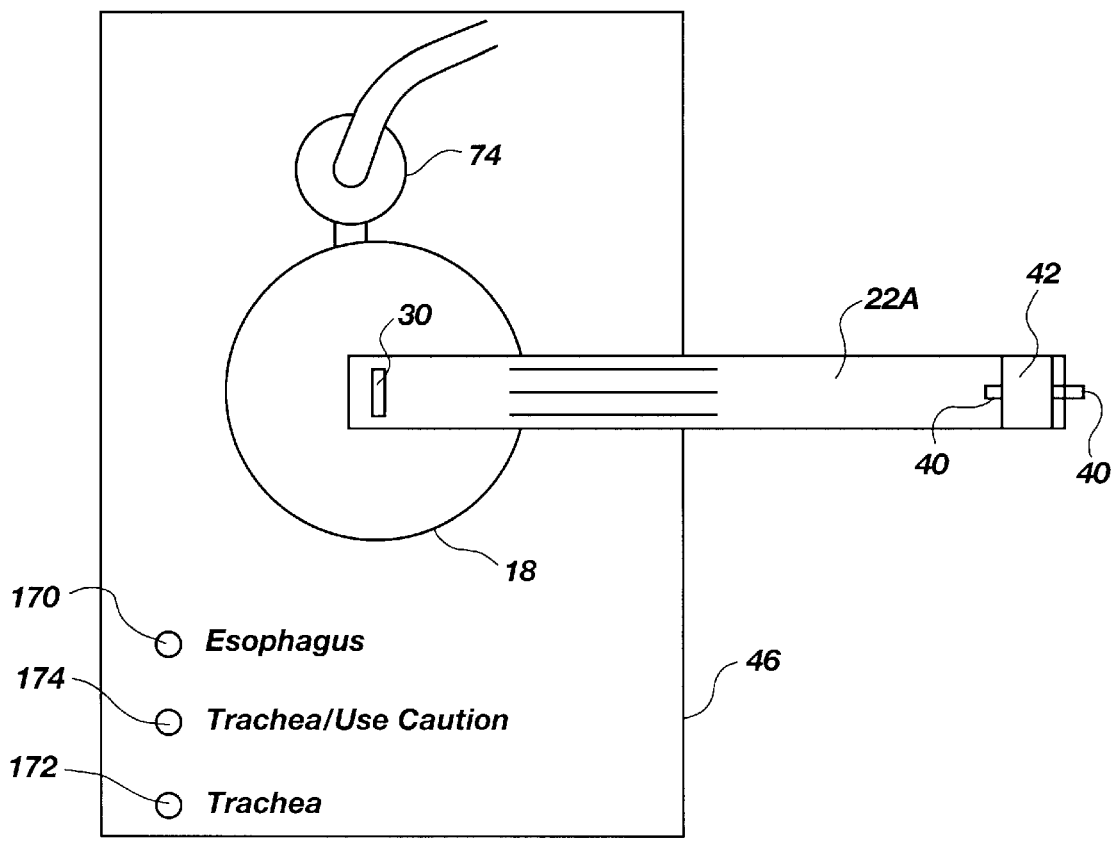
FIG. 8A is a top view of the intubation detection system of FIG. 1 including a portion of indication circuitry.

Analyzing circuitry 138 controls indication circuitry 150. Referring to FIG. 8A, the top of chassis 46 includes three light emitting diodes (LEDS) 170, 172, and 174, which are examples of elements of indication circuitry 150. LEDS 170, 172, and 174 may be labelled "ESOPHAGUS", "TRACHEA", and TRACHEA/USE CAUTION", respectively. Of course, various other labels could be used, and indication circuitry 150 could include other visual and/or audio means, such as a speaker, head phones, ear plug, liquid crystal display, mechanical indicator, including another of the various indicators described below in this specification or a combination of them. Indication circuitry 150 includes necessary drivers to drive LEDs and/or other indicators. The LED may have different colors. For example, LED 170 could be red, LED 172 could be green, and LED 174 could be yellow. A malfunction could be indicated by yet another LED lighting or by, for example, blinking of the LEDs.

Depending on the nature of signal conditioning circuitry 136 (e.g. the speed of an analog to digital converter), analyzing circuitry 138 may receive a great deal of data regarding pressure at transducer 130, or some lesser amount. Analyzing circuitry 138 may consider all of the data it receives or less than all of the received data. For example, under a simple algorithm, analyzing circuity 138 could merely look at the pressure at time 0.1 and at time 0.5 seconds. If the difference in the pressure at time 0.1 and the pressure at time 0.5 is less than a first threshold, analyzing circuitry 138 could cause LED 170 to be lit. If the difference in pressures at times 0.1 and 0.5 is greater than the second threshold, analyzing circuitry 138 could cause LED 172 to be lit. If the difference in pressures at times 0.1 and 0.5 is between first and second thresholds, analyzing circuitry 138 could cause LED 174 to be lit.

Other more complicated algorithms could be used by analyzing circuitry 138. For example, such algorithms could include considering more than two points or using curve fitting analysis. When curve fitting analysis is used, data could be collected and considered at a later time. These may be particularly useful with curves like curve 168. Optional computer, printer, and/or memory 156 may be useful for more complicated analysis, and for determining thresholds or other considerations for use in designing or programming analyzing circuitry 138 for use in the field.

Figure 8B:
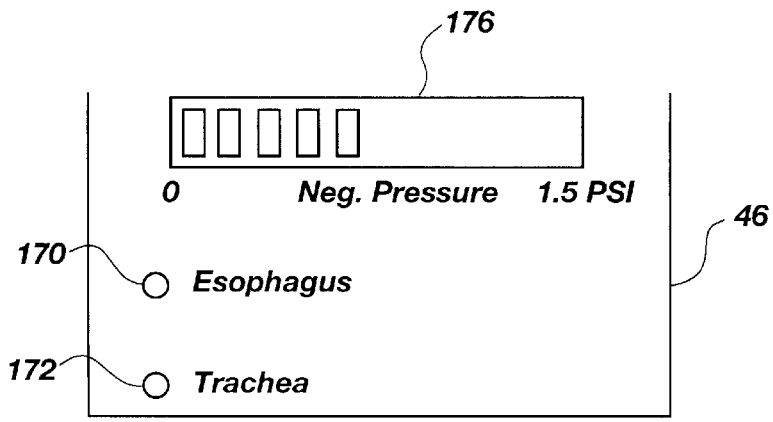
FIG. 8B is a portion of the top view of the intubation detection system of FIG. 1 with alternative indication circuitry.

FIG. 8B shows only a portion of the top of chassis 46, in which indication circuitry 150 includes only two LEDs, LED 170 and 172. In such a case, LED 172 could be lit if either of the second or third conditions is met (i.e., the conditions that cause either LED 172 or 174 of FIG. 8A to be lit). FIG. 8B also shows an optional bar graph 176 that indicates the amount of negative pressure at any given time. Graph 176 (or a similar indicator) may be used in connection with other indicators (e.g., in FIGS. 8A or 8C) and may provide useful information to the clinician.

Figure 8C:
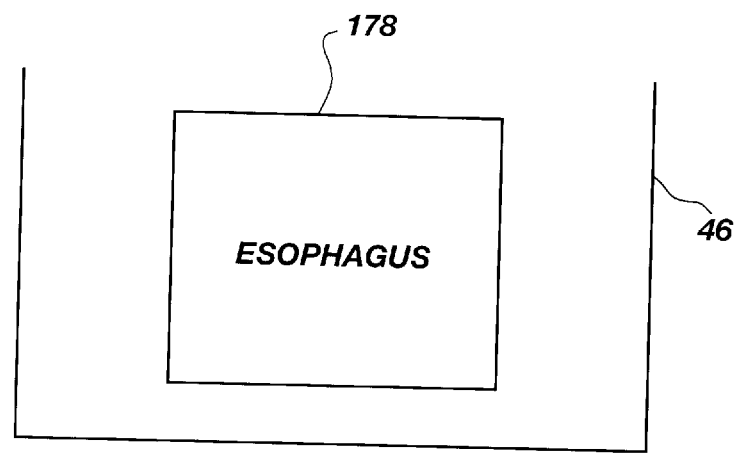
FIG. 8C is a portion of the top view of the intubation detection system of FIG. 1 with another alternative indication circuitry.

FIG. 8C shows only a portion of the top of chassis 46 and illustrates a display 178 (e.g., a back lit liquid crystal display) that may display various things. For example, display 178 could display the words such as words that appear by the LEDS of FIG. 8A or "MALFUNCTION" Display 178 could also display words such as one or more of endotracheal tube obstruction, morbid obesity, pulmonary edema, mainstem bronchus intubation, severe bronchospastic, or obstructive lung disease. Display 178 could display a curve like those of FIG. 7.

FIG. 6 illustrates a trigger 158 that when actuated provides an electrical signal to analyzing circuitry 138. The embodiment of FIG. 5 (and other embodiments) may include trigger 158, and the embodiment of FIG. 6 is not required to. Trigger 158 may be actuated by movement of lever 22A, plunger seal 124, the finger of a clinician, or some other means. Trigger 158 may include a switch and/or magnetic piece, or other circuitry. Trigger 158 may have particular usefulness in an embodiment that does not include flow restrictor 74. In the embodiment of FIG. 5 without flow restrictor 74, if tip 112 is in the trachea, there may be no change in pressure. If analyzing circuitry does not see a change in pressure within a certain amount of time after actuation of trigger 158, analyzing circuitry may cause LED 172 to be lit. If a change in pressure is detected, analyzing circuitry may cause LED 174 or another LED to be lit. In the embodiment of FIG. 6, the amount of flow through transducer 134 may differ depending on whether tip 112 is in the esophagus or the trachea. The presence or absence of flow restrictor 74 may influence the level of flow. (If flow restrictor 74 is not used, tubes 76 and 84 could be one tube.) Analyzing circuitry 138 may light the appropriate LED in response to the flow. If there is no flow in a particular case, analyzing circuitry 136 may consider the length of time following actuation of trigger 158. Again, it is noted that trigger 158 is optional. If trigger 158 is not used, analyzing circuitry 138 could begin analyzing upon, for example, a sudden increase in negative pressure.

The Mityvac includes a one-way valve 66 with a cover that allows air to leave chamber 120 when plunger seal 124 is lowered. The cover prevent debris from entering the one-way valve. The Mityvac also includes an optional release valve 68 that is actuated by a release lever 72.

Figure 9:
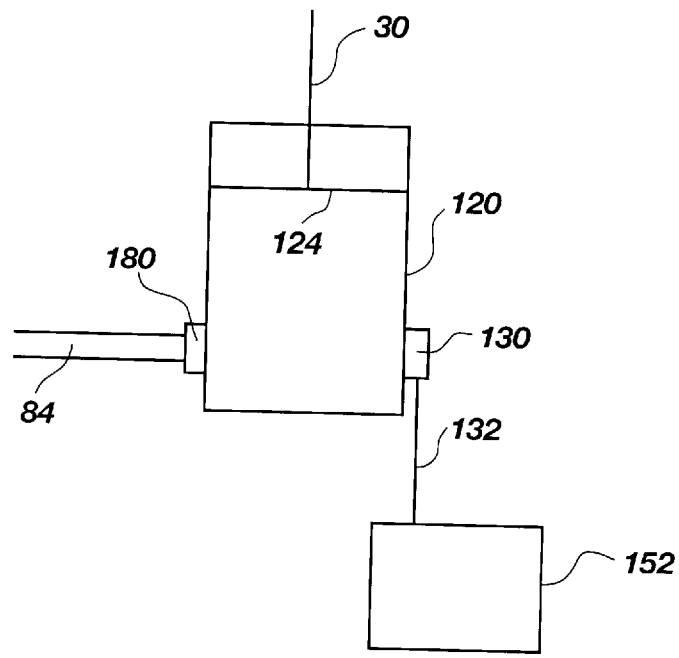
FIG. 9 is a partially schematical and partially block diagram representation of another alternative intubation detection system according to the present invention.

FIG. 9 shows an alternative arrangement to that of FIG. 5 in which transducer 130 and a flow restrictor 180 are attached directly to chamber 120. Transducer 130 and flow restrictor 180 may be inside, outside, or partially inside and partially outside chamber 120.

Figure 10A:
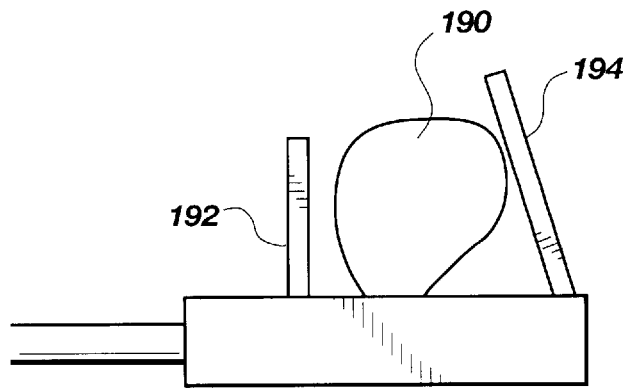
FIG. 10A is a side view of an alternative intubation detection system according to the present invention in which a bulb is fully inflated.
Figure 10B:
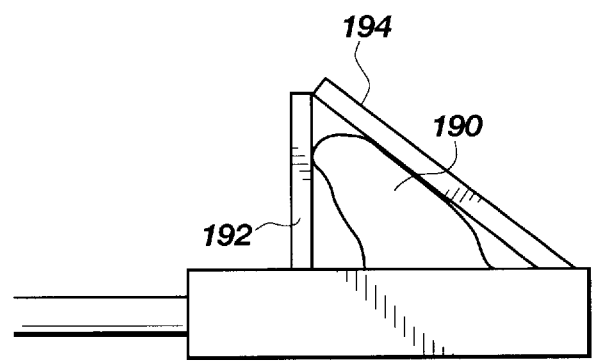
FIG. 10B is the system of FIG. 10A with the bulb partially deflated.

FIG. 10A shows a system employing a bulb 190 as a pressure changing source. The system may include (but is not required to include) a locking structure 192 and a movable element 194. As shown in FIG. 10B, movable element 194 may compress bulb 190. Movable element 194 may be locked against locking structure 192 to hold the volume of bulb 190 constant. When the bulb is released from a partially deflated position (as in FIG. 10B) to an inflated position (as in FIG. 10A), the volume increases. The increase in the volume of the bulb is analogous to the increase in volume of chamber 120.

Figure 10C:
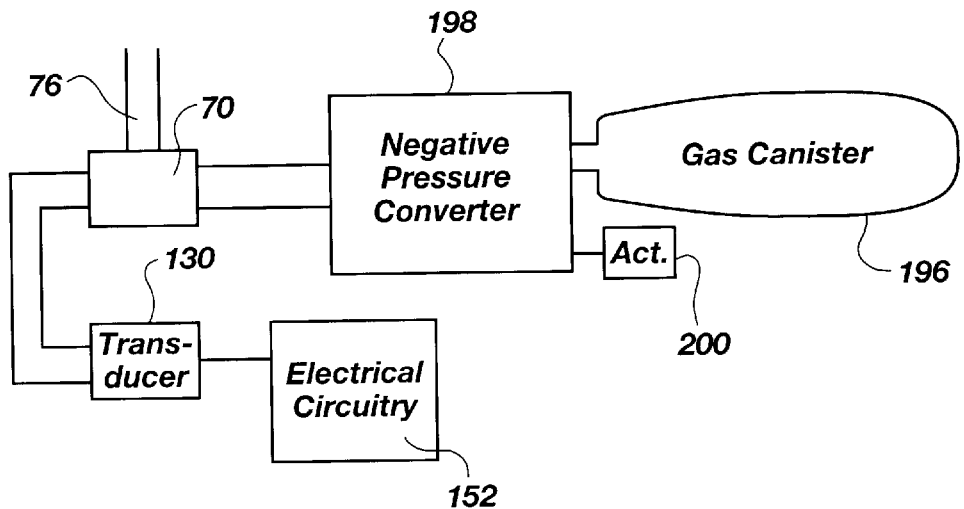
FIG. 10C is a partially schematical and partially block diagram representation of another alternative intubation detection system according to the present invention.

FIG. 10C shows another alternative intubation detection system in which a gas canister 196 (such as a $CO_2$ cartridge) provides pressure to a negative pressure converter 198 in response to activation of an actuator 200, which may be merely a button. Negative pressure converter 198 provides a negative pressure in response to receiving pressure from canister 196. Transducer 130 provides an electrical signal in response to the resulting pressure changes. A flow transducer could also be used.

Figure 10D:
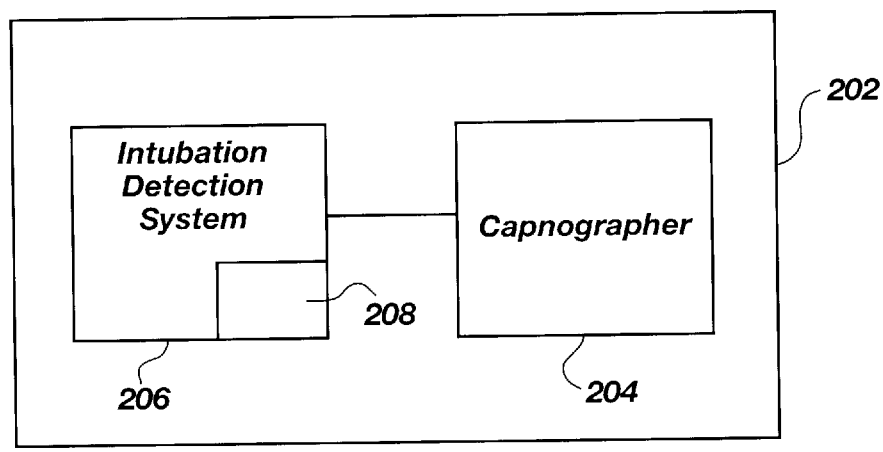
FIG. 10D is a block diagram representation of an alternative intubation detection system according to the present invention including a capnographer.

FIG. 10D shows a intubation system 202 in which a capnographer 204 is used in combination with an intubation detection system 206 of a type the same as or similar to those described in connection with one or more of FIGS. 1–10C. Capnographers include the ability to detect $CO_2$ with high precision. At the present time, capnographers are typically fairly expensive and therefore system 202 would be more likely to be used in hospitals or research settings, than in a remote emergency setting.

Intubation detection system 10 is preferably portable for use in emergency settings in the field and inside medical facilities. However, it may also be attached to an object, such as a table. Intubation detection system 10 is not only useful for gathering data about a specific person in an emergency setting, but also may be used as a data gathering tool.

Intubation detection system 10 might be called an esophageal intubation detection system because it detects when the endotracheal tube is in the esophagus.

Directional terms such as top, bottom, up, down are arbitrary. The volume changing device of FIG. 1 could be turned to a different directional orientation and still be within the scope of the invention.

An intubation detection system according to the present invention may include a port to receive the tip of the endotracheal tube for self leak testing.

B. Systems Including a Syringe

1. Embodiments of Detectors and Audio Indicators

Figure 11:
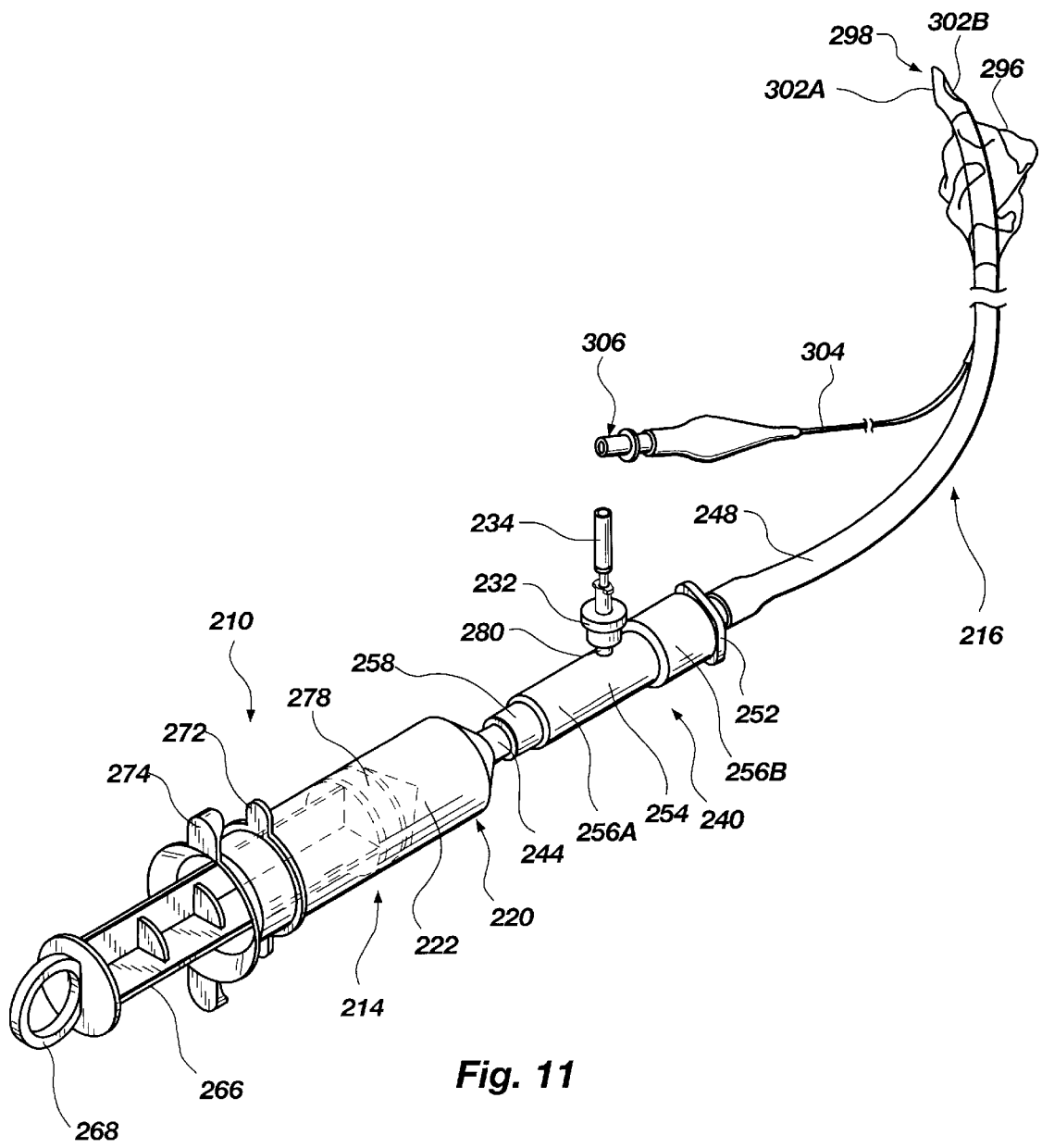
FIG. 11 is a perspective view of an esophageal intubation detector including an audible indicator and connected to an endotracheal tube.
Figure 12:
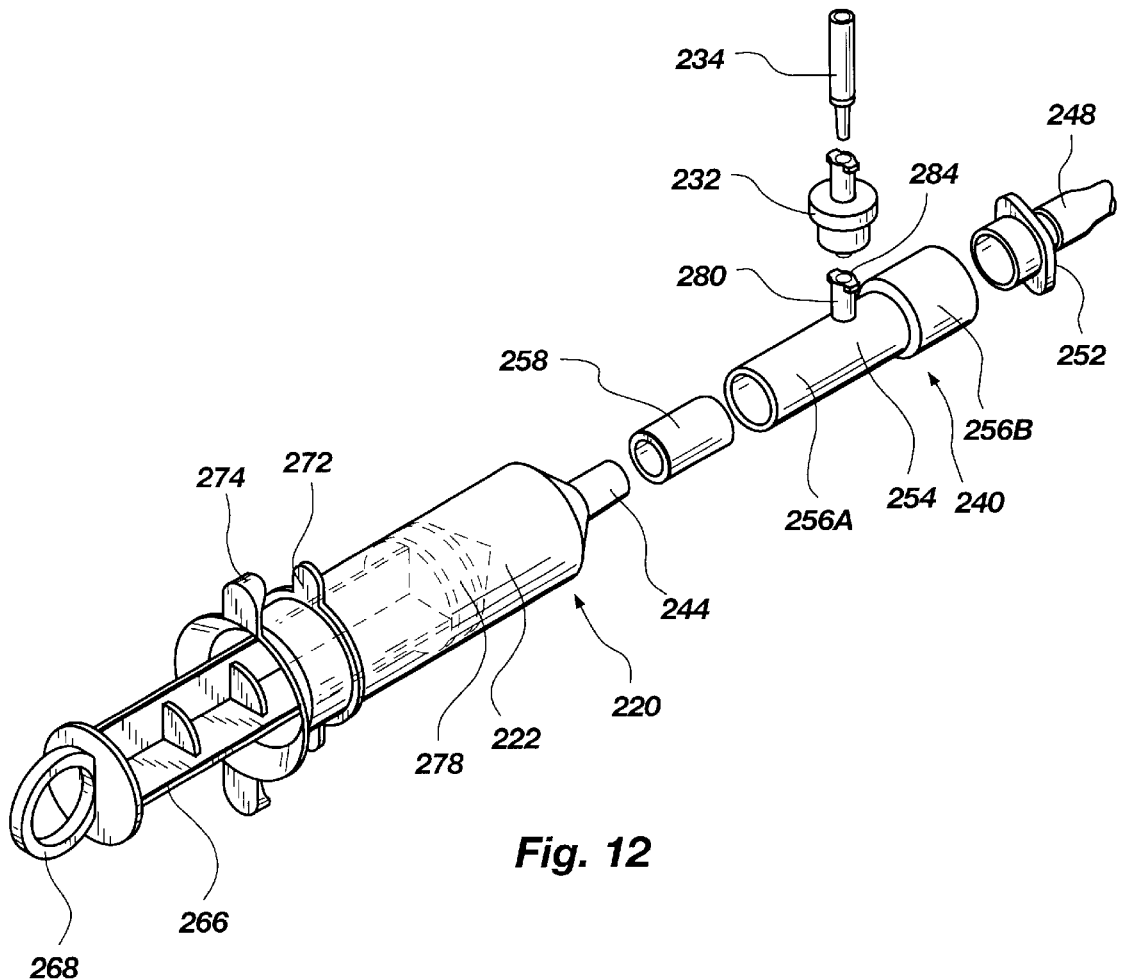
FIG. 12 is an exploded view of the esophageal intubation detector of FIG. 11 and a portion of the endotracheal tube.

Referring to FIGS. 11 and 12, in a first embodiment of the present invention, an esophageal intubation detection system 210 includes an esophageal intubation detector 214 and an endotracheal tube 216. In this first embodiment, esophageal intubation detector 214 includes a syringe such as standard catheter tip syringe 220 and an adapter 254 on which an indicator is positioned.

As described herein, a variety of indicators may be used. In the embodiment of FIGS. 11 and 12, the indicator is an audible indicator 232. Audible indicator 232 is shown with an optional sound enhancer 234 which increases the loudness of the sound from audible indicator 232. The length and diameter of sound enhancer 234 is chosen such that the sound in the combination of audible indicator 232 and sound enhancer 234 obtains resonant frequency. This results in a significant increase in the decibel output of the indicator, making it easily detected by the human ear. Details of audible indicator 232 are provided in FIGS. 14A and 14B below. Other audible indicators are shown in FIGS. 17, 19A, 19B, and 26.

Figure 13:
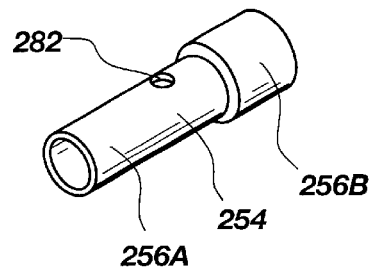
FIG. 13 is a perspective view of an adapter of the esophageal intubation detector of FIG. 11.

Referring to FIGS. 11–13, esophageal intubation detector 214 is connectable to endotracheal tube 216 by means of an adapter 240. It is contemplated that esophageal intubation detector 214 and endotracheal tube 216 may be sold separately or together, and if sold together, in a connected or disconnected condition.

Adapter 240 includes a hollow two-diameter adapter 254 and a connection tube 258. Two-diameter adapter 254 includes sections 256A and 256B. One end of connection tube 258 is connected over syringe tip 244 and the other end of connection tube 258 is connected inside section 256A of two-diameter adapter 254. Of course, adapter 240 could be comprised of a greater or fewer number of components than two-diameter adapter 254 and connection tube 258. Further, it is not necessary that a two-diameter adapter be used. It is preferred that connection tube 258 is connected between syringe tip 244 and section 256A in a tight fit to prevent separation and leakage. The use of heat during assembly may facilitate the tight fit. In actual use, connection tube 58 may be completely covered by one end of section 256A, as opposed to that illustrated in FIG. 11.

Syringe 220 includes a barrel 222 and a plunger 266 having a plunger seal 278 (shown inside barrel 222). Plunger 266 may include a ring handle 268, and syringe 220 may include handles 272 and 274 for ease in moving plunger 266.

One version of endotracheal tube 216 includes a tube 248 and an end adapter 252 at one end of tube 248. Endotracheal tube 216 includes an inflatable balloon 296 and a tip 298 with holes 302A and 302B. Balloon 296 may be inflated through a tube 304 and connection port 306. Of course, the details of endotracheal tube 216 could be different without departing from the present invention. Endotracheal tube 216 may be the same as endotracheal tube 90 (in FIG. 4).

Before intubation, plunger 266 is positioned so that plunger seal 278 is near syringe tip 244. Under one procedure, at the time of intubation, a clinician inserts tip 298 of endotracheal tube 216 into the throat of the patient. After initial intubation, the clinician connects section 256B over end adaptor 252 of endotracheal tube 216. The clinician then pulls plunger 266 away from syringe tip 244. Under another procedure, section 256B is connected to end adaptor 252 prior to initial intubation.

Referring to FIGS. 11 and 12, in a preferred embodiment, a hollow luer lock stem 280 is connected to section 256A of two-diameter adapter 254. Audible indicator 232 is connected to luer lock stem 280. Section 256A has an orifice 282 (shown in FIG. 13). Stem 280 has an orifice 284 that is open with respect to orifice 282 allowing passage of air between a lower portion of audible indicator 232 and the hollow portion of two-diameter adapter 254. Stem 280 may be originally molded or otherwise formed as an integral portion of two-diameter adapter 254 or may be inserted into orifice 282 and melted or glued thereto. Stem 280 may project partially through orifice 282. As used herein, referring to the indicator as being positioned over the orifice does not preclude the indicator from being partially inserted through the orifice.

Figure 14A:
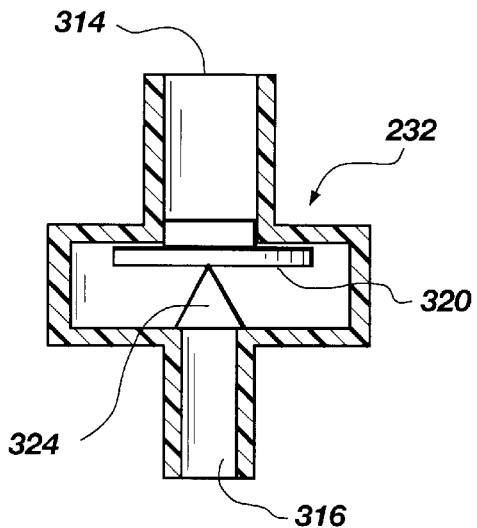
FIG. 14A is a side sectional view of an audible indicator.
Figure 14B:
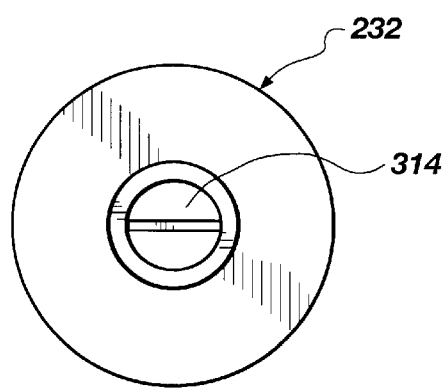
FIG. 14B is a top view of the audible indicator shown in FIG. 14A.

FIGS. 14A and 14B show side and top views of audible indicator 232. Audible indicator 232 includes an orifice 314 and an orifice 316, which are aligned with orifice 284 (such as by any of the ways described in connection with stem 280 and orifice 284). When the difference in air pressures in orifice 314 and 316 equals a "crack pressure," a disk 320 vibrates on a stand 324 and thereby produces a sound. Merely by way of example, and not limitation, the crack pressure of audible indicator 232 is minus 1.5 to minus 5.0 psi. Various indicators will have different crack pressures.

As used herein, the volume in barrel 222, adapter 240, and tube 248 between syringe seal 278 and tip 298 of endotracheal tube 216 is referred to as the "system volume." The air pressure (psi) in barrel 222, adapter 240, and tube 248 between syringe seal 278 and tip 298 is referred to as the "system pressure." If intubation is proper, the system pressure remains essentially constant as plunger 266 is pulled away from syringe tip 244. Accordingly, the pressure differential across audible indicator 232 remains essentially constant.

On the other hand, if intubation is not proper, tip 298 becomes occluded, and the system pressure decreases as plunger 266 is pulled away from syringe tip 244. The system pressure decreases until it is less than the crack pressure of audible indicator 232. Air then passes about disk 320 causing it to vibrate. The vibration of disk 320 produces a sound indicating to the clinician that intubation may be improper. The crack pressure is reached when a significant pressure differential is achieved across audible indicator 232. As used herein, a significant pressure differential is one that activates the indicator.

Figure 15:
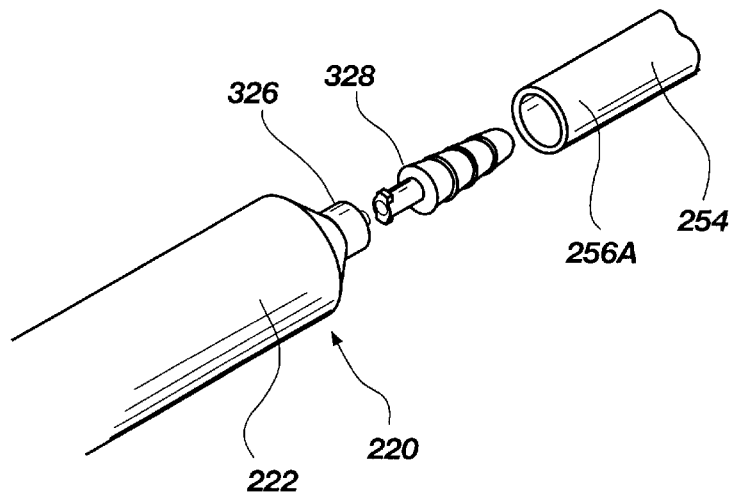
FIG. 15 is a perspective view of a luer lock structure for connecting the syringe to the adapter.

FIG. 15 illustrates an alternative structure for joining syringe barrel 222 to adapter 254. In the embodiment of FIG. 15, a luer lock syringe tip 326 connects to a luer lock connection adapter piece 328, which fits inside section 256A of adapter 254. Luer lock syringe tip 326 may be connected to luer lock connection adapter piece 328 prior to or after attempted intubation. The structure of FIG. 15 may be used with various embodiments of the esophageal intubation detection system, such as, for example, that of FIG. 11.

Figure 16A:
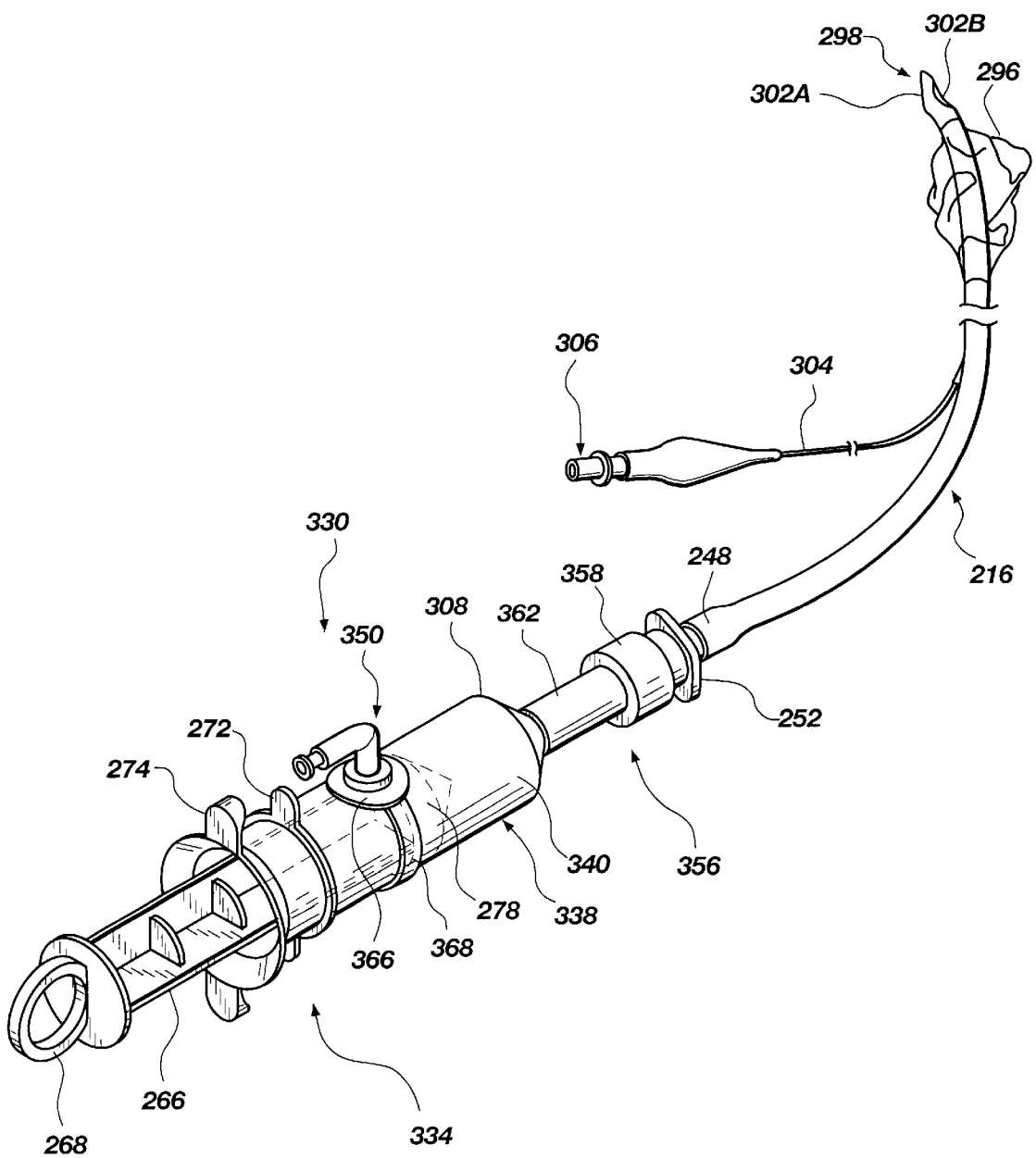
FIG. 16A is a perspective view of an alternative embodiment of an esophageal intubation detector including an alternative audible indicator and connected to an endotracheal tube.

Referring to FIGS. 16A and 16B, an esophageal intubation detection system 330 includes an esophageal intubation detector 334 and endotracheal tube 216 connected through an adapter 356. Esophageal intubation detector 334 includes a syringe such as a standard catheter tip syringe 338 having a barrel 340. (Alternatively, the luer lock structure of FIG. 15 could be used.) In contrast to orifice 284 in two-diameter adapter 254 (shown in FIGS. 11–13), esophageal intubation detector 334 in FIGS. 16A and 16B included an orifice 344 in barrel 340 over which an indicator is secured in place.

Figure 17:
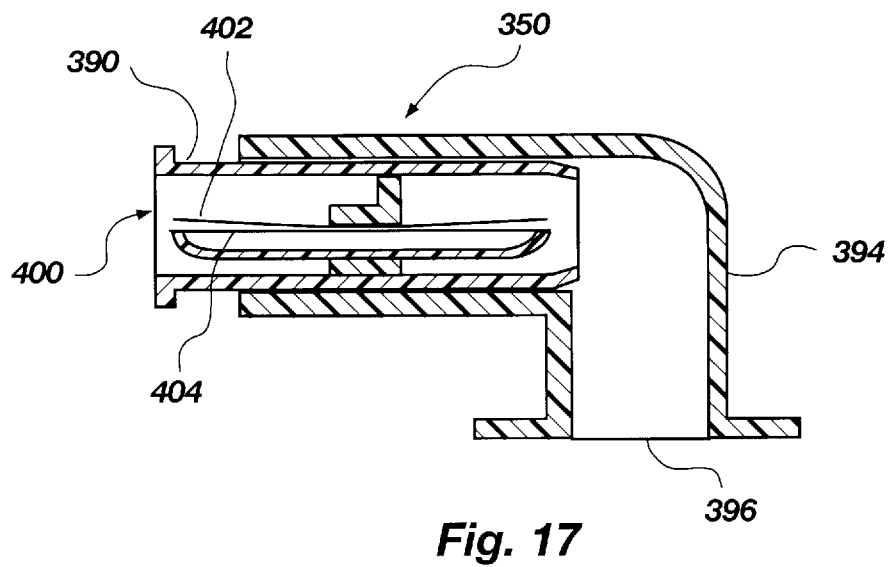
FIG. 17 is a side sectional view of the second embodiment of an audible indicator.

In FIGS. 16A and 16B, the indicator is an audible indicator 350, which is shown in detail in FIG. 17. Various other indicators, including those described and illustrated in detail in this specification could be used instead. As with the system of FIG. 11, if intubation is proper, tip 298 is in the trachea and the system pressure remains essentially constant as plunger 266 is pulled back. Accordingly, there is no pressure differential across indicator 350 even when syringe seal 278 passes orifice 344. By contrast, if it is in the esophagus, tip 298 becomes occluded and the system pressure decreases. When syringe seal 278 passes orifice 344, a significant pressure differential is created across indicator 350 causing activation of indicator 350 (i.e., indicator 350 makes a noise).

Indicator 350 may be held in place by a base 366 that is secured to barrel 340 over orifice 344 with a strap 368. Base 366 and strap 368 are preferably made of rubber or flexible silicone which fits around barrel 340 and forms a hermetic seal with barrel 340. Base 366 and strap 368 may be formed or joined as a unit. Alternatively, base 366 may be glued, welded, or otherwise attached to barrel 340. Orifice 344 may have a stem (similar to luer lock 280 in FIG. 11) connected to it.

Referring to FIGS. 16A and 16B, esophageal intubation detector 334 is connectable to endotracheal tube 216 by means of an adapter 356. Adapter 356 includes an endotracheal tube adapter 358 and a connection tube 362. One end of connection tube 362 is connected to syringe tip 244 and the other end of connection tube 362 is connected to endotracheal tube adapter 358.

Adapters between the syringe and endotracheal tube are desirable in the case in which typical syringe tips are not suitable for connection directly with typical endotracheal tubes. However, the invention is not restricted to systems with adapters. For example, the syringe (or other volume changing devices described below) and/or the endotracheal tube may be constructed such that an adapter is not necessary. That combination could be sold as individual parts or as an integral unit for use by clinicians. The indicator could be attached to the syringe (or other volume changing devices described below) and/or the endotracheal tube.

FIG. 17 shows a cross-section of a side view of audible indicator 350 (shown in FIGS. 16A and 16B), which includes a whistle 390 in a housing 394. Housing 394 includes an orifice 396 which may be aligned with and sealed around (or otherwise formed with respect to) orifice 344. Whistle 390 includes an orifice 400, and reed elements 402 and 404, which create a noise when air passes through them. When tip 298 is occluded and plunger seal 278 passes by orifice 344, air suddenly passes through orifice 400 toward orifices 396 and 344 creating a noise.

Figure 18:
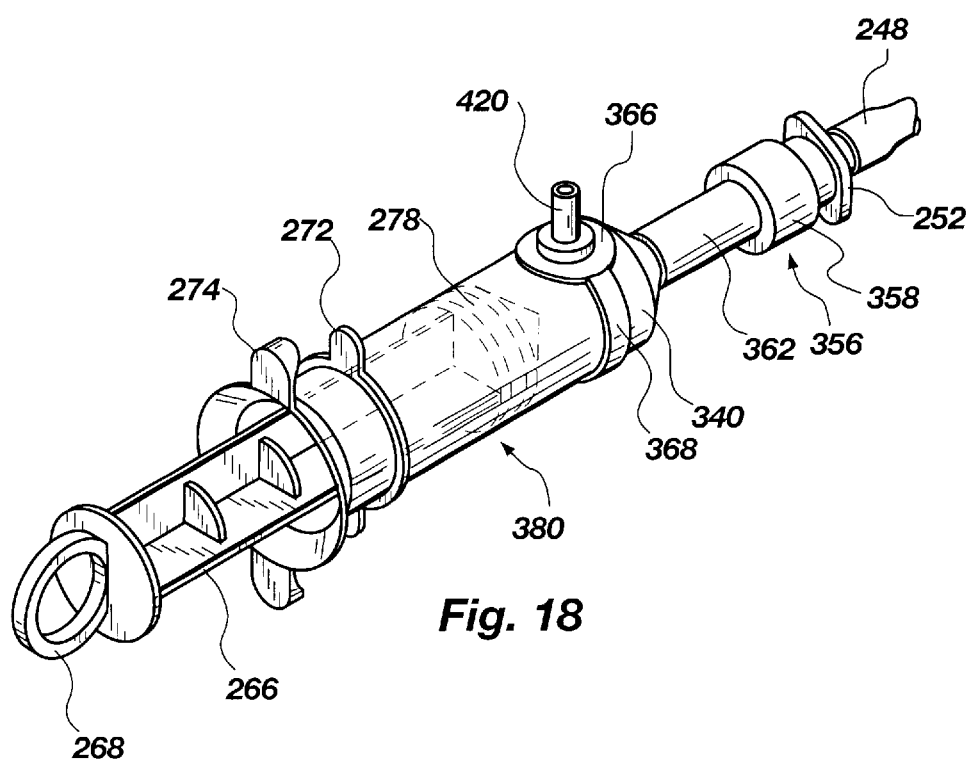
FIG. 18 is a perspective view of yet another esophageal intubation detector (like that shown in FIGS. 16A and 16B except the orifice is closer to the syringe tip) that includes another embodiment of an audible indicator.

FIG. 18 is a perspective view of a third embodiment of an esophageal intubation detector 380, which is like that of the second embodiment shown in FIGS. 16A and 16B except orifice 344 is closer to the syringe tip. There are some tradeoffs in the choice of positioning orifice 344 with respect to tip 244. The following are factors to consider. First, at least some significant negative pressure is required to properly activate an indicator (e.g., to be sufficiently loud to be heard). This would suggest moving the orifice 344 farther from syringe tip 244 to make a loud noise. Second, the farther orifice 344 is from syringe tip 244, the more effort is required to pull plunger 266 and the greater the reduction in pressure and/or the longer the reduction in pressure. Experimentation may provide information regarding how far orifice 344 should be from tube tip 244. It is expected, however, that a fairly loud noise can be generated with orifice 344 being fairly near tube tip 244 (as shown in FIG. 18).

Figure 19A:
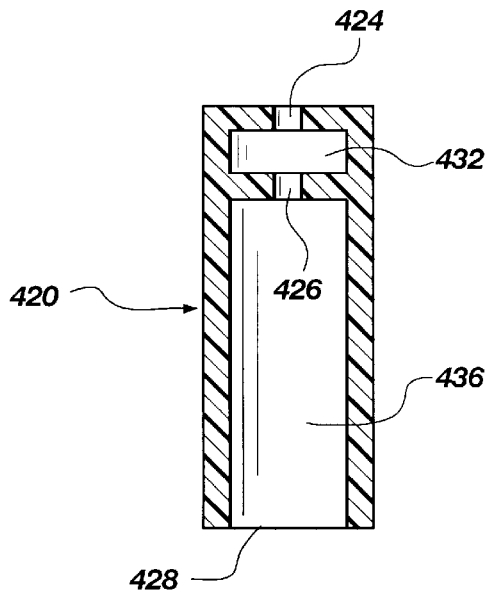
FIG. 19A is a side sectional view of an audible indicator.
Figure 19B:
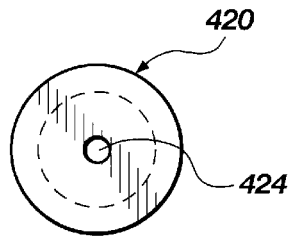
FIG. 19B is a top view of the audible indicator shown in FIG. 19A.

FIGS. 19A and 19B show side and top views of an audible indicator 420 (shown in FIG. 18), which is a third embodiment of an audible indicator. Audible indicator 420 includes small diameter orifices 424 and 426, and a larger diameter orifice 428, which is aligned with and sealed around (or otherwise joined with) orifice 344. Audible indicator 420 includes cavities 432 and 436. If tip 298 is occluded a negative pressure is created. When plunger seal 278 passes by orifice 344, air passes through orifices 424 and 426 toward orifices 428 and 344 causing a sound to be produced. Indicator 420 could be positioned on an adapter, such as in FIG. 11.

Figure 20:
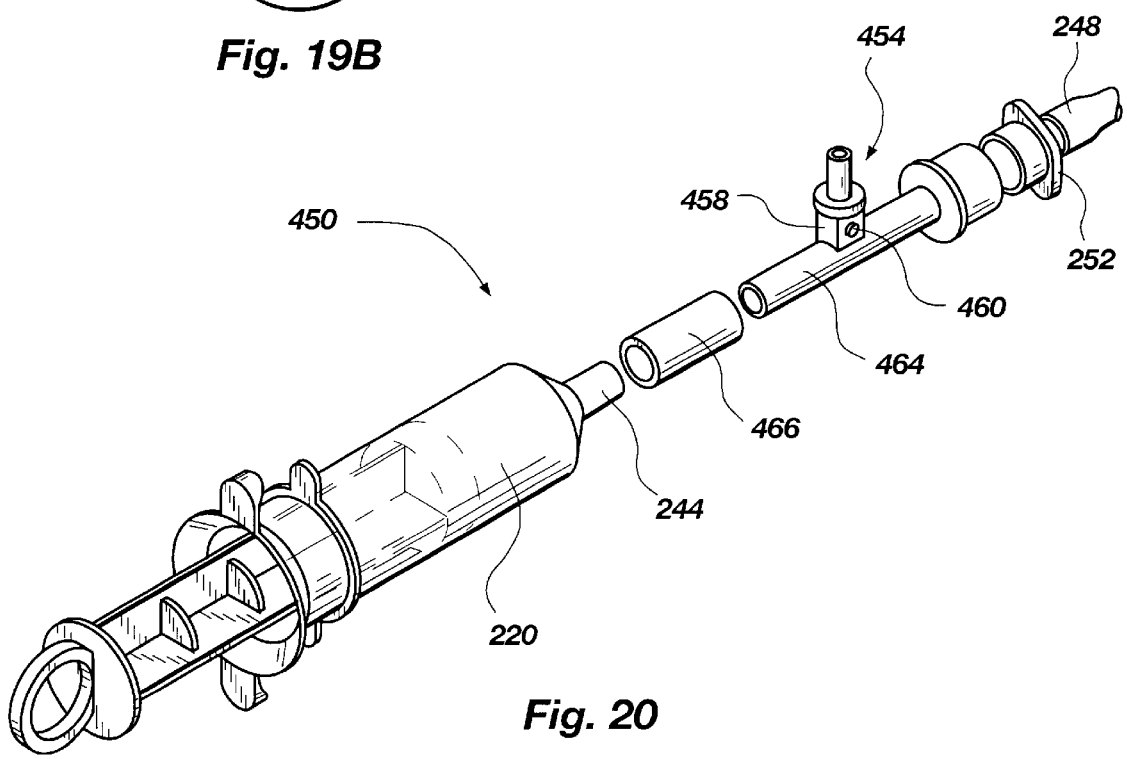
FIG. 20 is an exploded view of another esophageal intubation detector including another audio indicator and connected to an endotracheal tube.

FIG. 20 illustrates esophageal intubation detector 450, which is an alternative arrangement of esophageal intubation detector 214 in FIG. 11. An indicator 454 (which may be the same as audible indicator 420 or a visual indicator) is positioned on a switch housing 458 having a control switch 460. After the system pressure is significantly negative due to pulling back the plunger, the clinician presses a button in control switch 460 allowing air to flow through indicator 454. Activation of control switch 460 is analogous to the crack pressure of indicator 232. An advantage of using switch 460 is that the clinician will know when to expect a noise or visual indication. This may be useful in situations of distracting noise or light. FIG. 20 also illustrates an alternative adapter arrangement including adapter 464 and connector element 466.

Figure 21:
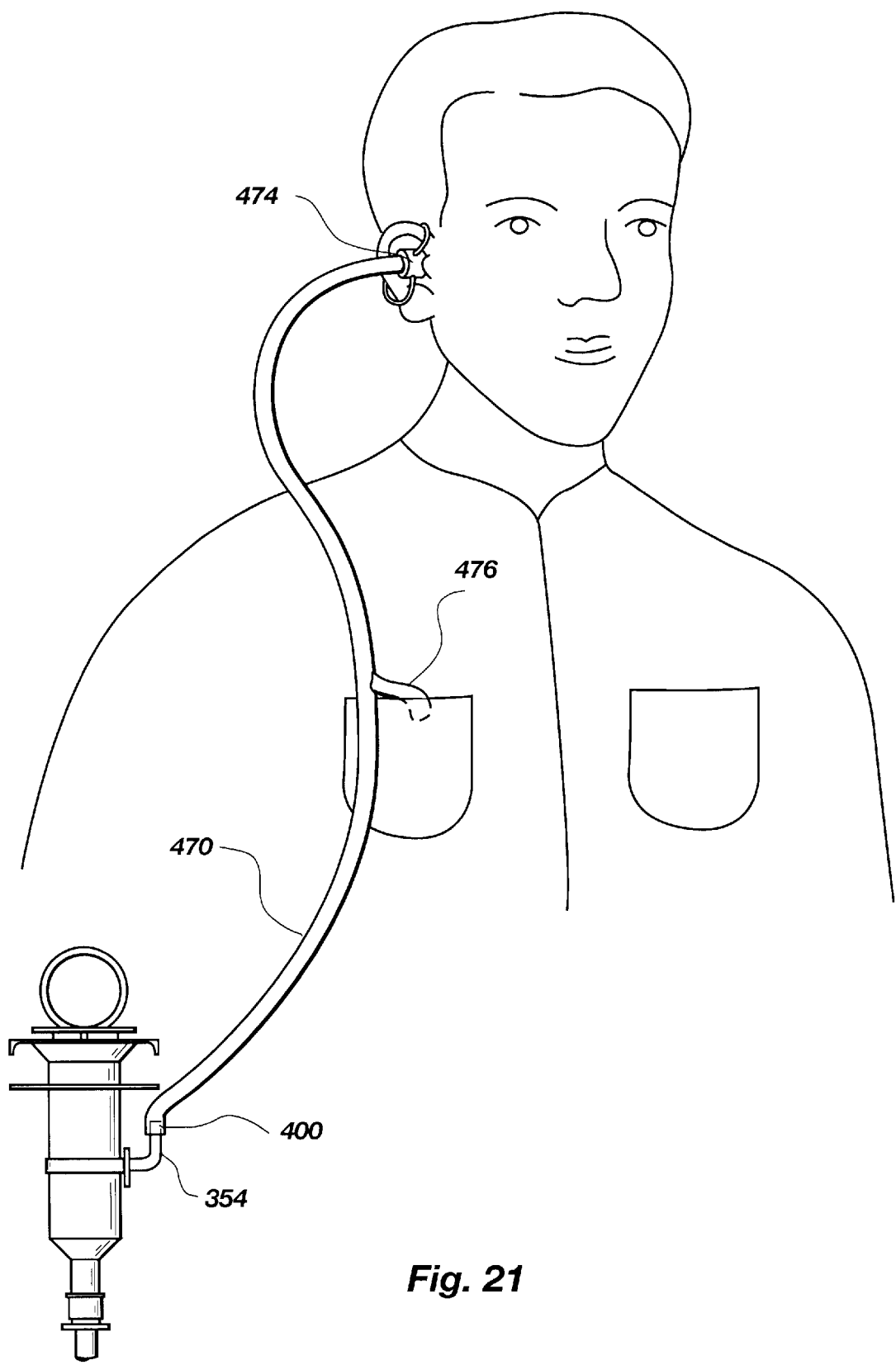
FIG. 21 is a perspective view of an extension tube that connects an audible indicator of an esophageal intubation detector to an ear piece fitting into the ear of a clinician.

Emergency settings in which the esophageal intubation detection systems described herein may be used are often noisy. Referring to FIG. 21, a tube 470 is connected between orifice 400 of audible indicator 354 and an ear piece 474 clipped to the ear of a clinician. A clip 476 may be clipped to the clothing of the clinician to prevent ear piece 474 from being pulled from the clinician's ear. Of course, tube 470 may be used in connection with the other audible indicators.

2. Visual Indicators

As an alternative or addition to an audible indicator, a visual indicator may be used to provide an indication of whether intubation is proper.

Figure 22A:
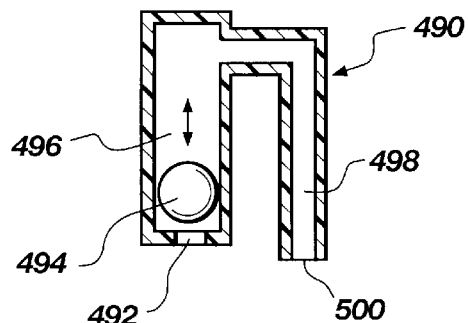
FIG. 22A is a side sectional view of a visual indicator.
Figure 22B:
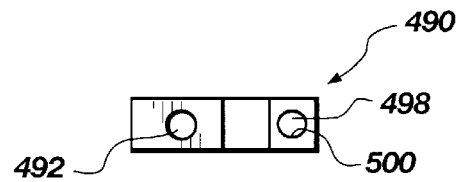
FIG. 22B is a top view of the visual indicator shown in FIG. 22A.

FIGS. 22A and 22B show side and top views of a transparent visual indicator 490, which is a first embodiment of a visual indicator. Visual indicator 490 includes a cavity 496 between an orifice 492 and a tube 498. Tube 498 includes an orifice 500, which is aligned with and sealed around (or otherwise connected to) an orifice in a detection system, such as orifice 482 in FIG. 13 or orifice 344 in FIG. 16B. When a significant pressure differential is created between orifice 492 and orifice 500 (because holes 302A and 302B in tip 298 are occluded), air passes through orifice 492 and toward orifice 500 causing a ball 494 to rise, indicating that tube tip 498 is in the esophagus rather than the trachea. Ball 494 may be made of or covered with glow in the dark material for ease of sight during low light conditions.

Figure 23A:
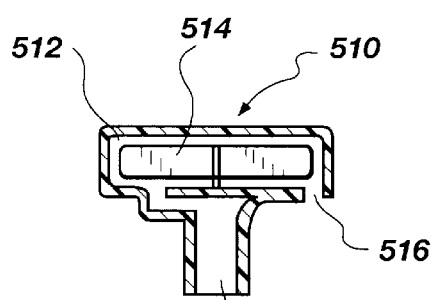
FIG. 23A is a side sectional view of another visual indicator.
Figure 23B:
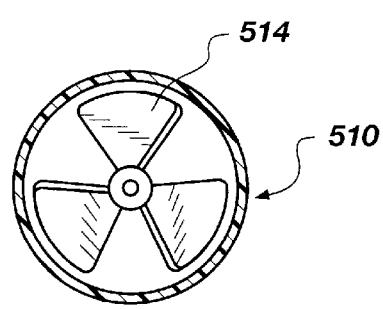
FIG. 23B is a top view of the visual indicator shown in FIG. 23A.

FIGS. 23A and 23B show side and top views of a visual indicator 510, which is a second embodiment of a visual indicator. Visual indicator 510 includes a cavity 512, in which a paddle wheel 514 is suspended, and orifices 516 and 518. Orifice 518 is aligned with and sealed around (or otherwise connected to) an orifice in a detection system, such as orifice 282 in FIG. 13 or orifice 344 in FIG. 16B. When a significant pressure differential is created between orifice 516 and orifice 518 (because holes 302A and 302B in tip 298 are occluded), air passes through orifice 516 toward orifice 518 causing paddle wheel 514 to spin indicating that intubation may have been in the esophagus rather than the trachea. Wheel 514 may be covered with glow in the dark material.

Figure 24A:
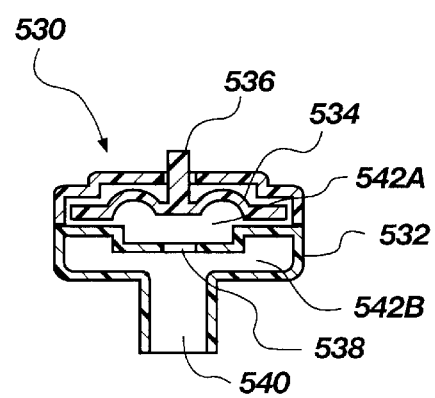
FIG. 24A is a side sectional view of another visual indicator.
Figure 24B:
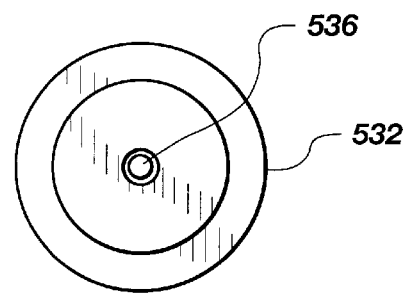
FIG. 24B is a top view of the visual indicator shown in FIG. 24A.
Figure 26:
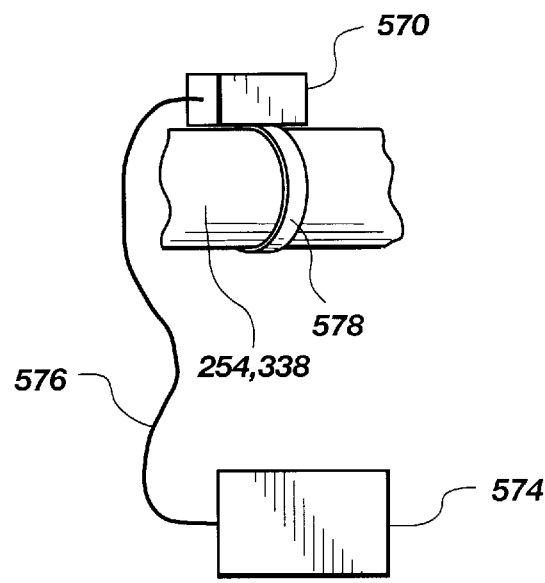
FIG. 26 shows a perspective view of an esophageal intubation detector having a transducer that provides a signal to a communication device.

Indicators 232, 350, 420, 490, and 510 are examples of vented indicators. These indicators are activated by a flow of air from the outside, through them and an orifice in a detection system, such as orifice 282 in FIG. 13 or orifice 344 in FIG. 16B. This flow of air will only occur if endotracheal tip 298 is occluded by the esophagus causing the system pressure to be negative, creating a significant pressure differential across the indicator. The indicators illustrated in FIGS. 24A, 24B, and 26 are examples of non-vented indicators. (It is expected that transducer 570 in FIG. 26 could be vented or non-vented.) Non-vented indicators are activated by the negative pressure causing a significant pressure differential across the indicator, but they do not allow air flow through the indicator.

FIGS. 24A and 24B show side and top views of a visual indicator 530, which is a third embodiment of a visual indicator. Visual indicator 530 includes a housing 532 that encloses a silicone diaphragm 534. An orifice 538 separates cavities 542A and 542B within housing 532. Silicone diaphragm 534 is connected to an indicator post 536. Visual indicator 530 includes an orifice 540, which is aligned with and sealed around (or otherwise connected to) an orifice in a detection system, such as orifice 282 in FIG. 13 or orifice 344 in FIG. 16B. When a significant pressure differential is created between the atmospheric pressure and the pressure at orifice 540 (because holes 302A and 302B in tip 298 are occluded), the pressure inside cavities 542A and 542B suddenly decreases causing silicone diaphragm 534 to pull indicator post 536 toward orifice 540, indicating that the tip of the endotracheal tube may have been in the esophagus rather than the trachea. Indicator post 536 may be made of or covered with glow in the dark material Alternatively, visual indicator 530 could be designed so that indicator post 536 pops up rather than down.

3. Audio and/or Visual Indicators

Figure 25:
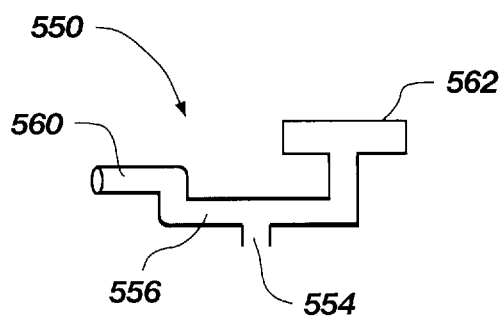
FIG. 25 shows a side view of a combined indicator including both audio and visual indicators.

FIG. 25 shows a combination audio and visual indicator 550. T-connector tube 556 includes an orifice 554, which is aligned with and sealed around (or otherwise connected to) an orifice in a detection system, such as orifice 282 in FIG. 13 or orifice 344 in FIG. 16B. T-connector tube 556 is connected to an audible indicator 560 (which may be any of the above-described audible indicators or another audible indicator) and a visual indicator 562 (which may be any of the above-described visual indicators or another visual indicator). Rather than using a connector tube 556, there could be two orifices, preferably at the same distance from syringe tip 244 (whether on the syringe or adapter), connected to two indicators.

Referring to FIG. 26, the indicator could be a transducer 570 connected to a communication device 574 through a wire 576. Transducer 570 could be activated in response to a change in pressure, a particular pressure differential across the transducer, a particular air speed, flow of air, or some other phenomenon. Communication device 574 could be an audio indicator (such as a loud speaker) and/or a visual display. The visual display could include a liquid crystal display (LCD) or light emitting diodes (LEDs). The LCD could display words describing the condition detected. Information that communication device 574 could provide includes the following: (1) tip 298 is in the esophagus, with the absence of the information indicating the contrary; (2) tip 298 is in the trachea, with the absence of the information indicating the contrary; or (3) tip 298 is in the esophagus or the trachea, depending on the particular situation at the time.

Transducer 570 could include a transmitter, and communication device 574 could include a receiver, such that wire 576 is not required.

Transducer 570 could be connected over an orifice in an adapter (for example, adapter 254 in FIG. 11), in a syringe (for example, syringe 338 in FIG. 16A), or another volume or pressure changing device (such as a bulb or bag described below). Communication device 574 could be also placed right on the adapter or syringe. Various means, such as glue or an optional strap 578 may be used to secure the transducer and/or communication device to the adapter, syringe, or other volume or pressure changing device.

Transducer 570 could include a sound detecting transducer placed over an audible indicator and connected to an amplifier and speaker to provide increased sound.

Transducer 570 could be vented or non-vented. Under one embodiment, if transducer 570 is non-vented, the pressure sensed by it will decrease as the plunger seal is pulled away from the syringe tip. At a pre-defined or particular negative pressure, the transducer will be triggered, indicating that tip 298 is improperly placed. If the transducer is vented, the achievement of this negative pressure will result in sudden flow of air through the orifice and a return in atmospheric pressure, which will also trigger the transducer and indicate improper endotracheal tube location.

An ear clip as in FIG. 21 may be used in connection with a transducer 570.

The preferred location of the indicator orifice (such as orifice 282 in FIG. 13 or orifice 344 in FIG. 16B) in the esophageal intubation detection system depends on the type of indicator used. If indicators requiring a predetermined negative pressure to activate such as indicators 232, 530 and 570 (described in FIGS. 14A, 14B, 24A, 24B, 26), the preferred location of the orifice will be overlying the adapter such as that shown in FIG. 11. This allows indicator activation at any time the system pressure drops low enough, regardless of the distance plunger 266 has been retraced. Indicators 350, 420, 480, and 510 (described in FIGS. 17, 19A, 19B, 22A, 22B, 23A, 23B) may also be placed in this location provided, that in preferred embodiments, they are connected to a pressure sensitive valve such as that used in indicator 232, which will not open until a predetermined (e.g., minus 1.5 to minus 5.0 psi) negative pressure is achieved. If they are used alone as described in FIG. 16B, then orifice 344 should be located on the syringe to allow sufficient negative pressure to be generated prior to orifice 344 being open to the inside of the system. This allows sufficient negative pressure to build up prior to activation of the indicator.

C. Bulb-Based Detection Systems

1. Evacuator Bulb

Figure 27A:
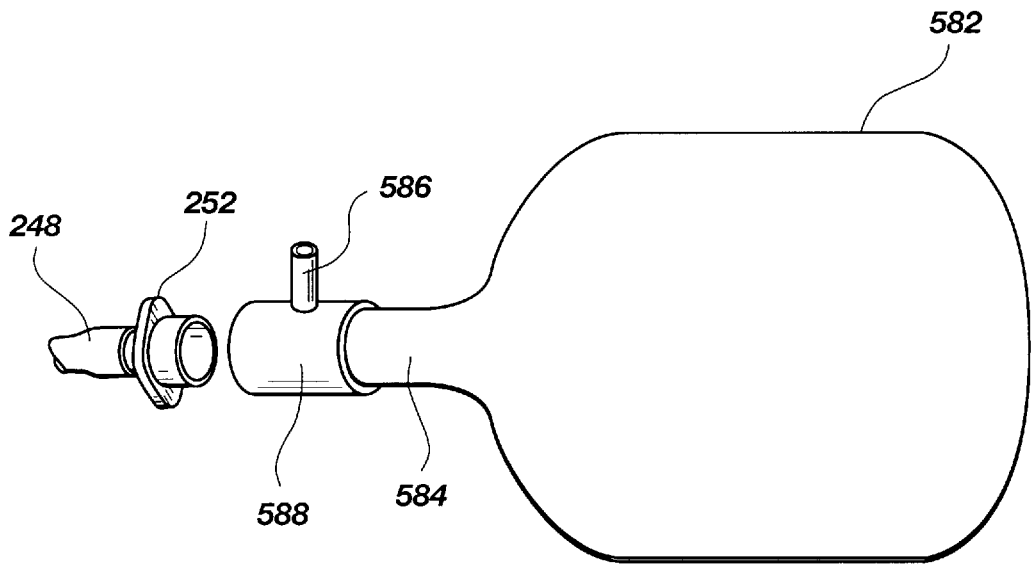
FIG. 27A shows a perspective view of an esophageal intubation detector including an evacuator bulb.

Although the esophageal intubation detector may comprise a syringe, it may use other sources of pressure changes such as a mechanized pump or evacuator bulb. Referring to FIG. 27A, a clinician may use evacuator bulb 582 to change the pressure in an endotracheal tube 248. Indicator 586, which may be any of the previously described indicators, is connected to an adapter 588 through an orifice. Before or after initial intubation, adapter 588 is connected to end adapter 252 at one end of tube 248.

Indicator 586 may also be connected to an orifice anywhere on the bulb where negative pressure is generated. Adapter 588 may be located anywhere on bulb 582 where negative pressure is generated. Adapter 588 is connected to evacuator bulb 582 either directly or by a connecting tube 584.

Figure 27B:
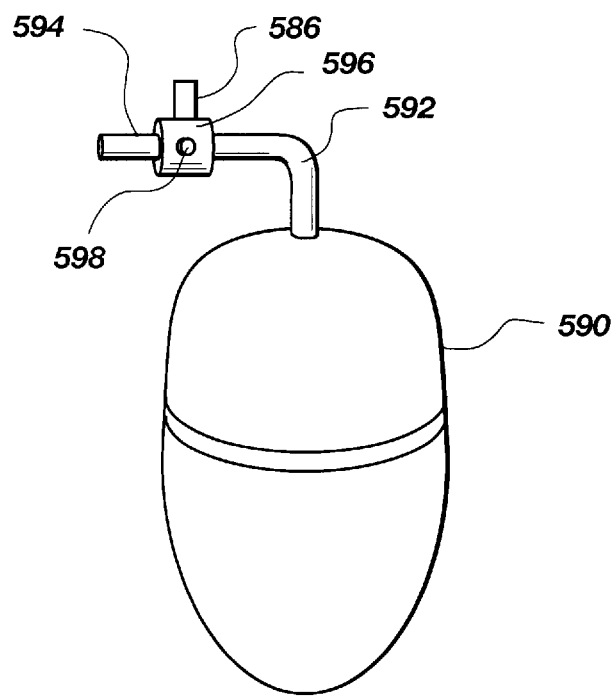
FIG. 27B shows a perspective view of an alternative embodiment of an esophageal intubation detector including an evacuator bulb.

FIG. 27B shows an alternative arrangement of the system of FIG. 27A. Referring to FIG. 27B, evacuator bulb 590 is connected through a tube 592 to a tube 594 through to a switch housing 596. Indicator 586 is connected to switch housing 596. A switch 598 may be used to control flow of air or pressure to which indicator 586 is exposed.

2. Resuscitator Bag

Figure 28A:
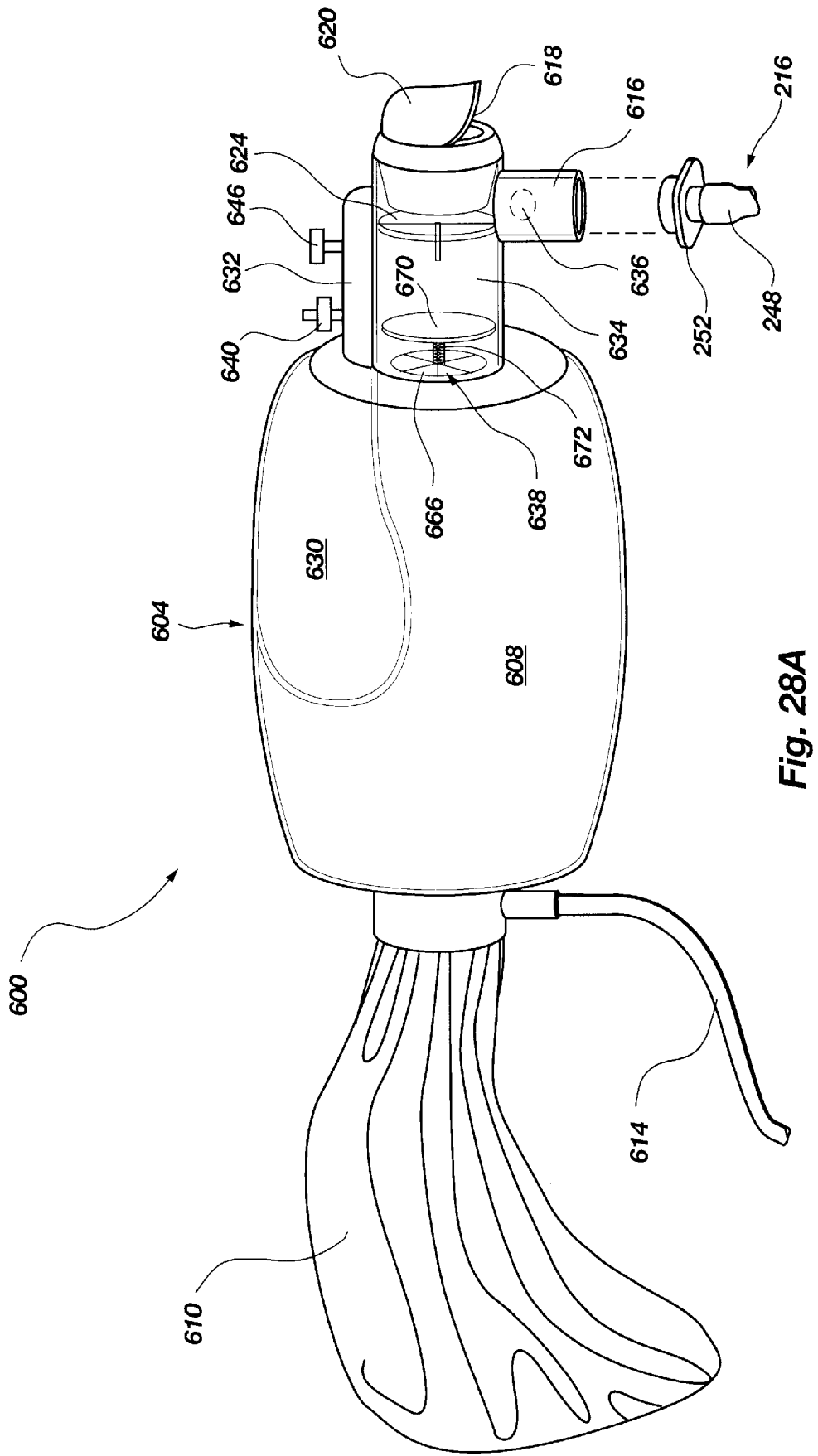
FIG. 28A is a side view of an intubation detector/ resuscitator system including an indicator.
Figure 28B:
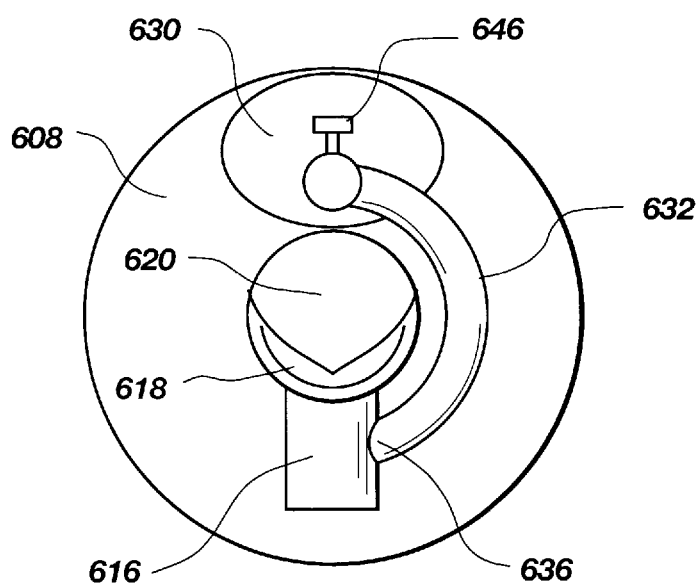
FIG. 28B is a front view of the intubation detector/ resuscitator system of FIG. 28A.

Referring to FIG. 28A (side view) and FIG. 28B (front view), in a preferred embodiment, an intubation detection system 600 includes an intubation detection/resuscitator bag 604. In a preferred embodiment, detection/resuscitator bag 604 includes standard, well known parts including a ventilating bag 608, an oxygen reservoir 610, an oxygen tube 614, an adapter 616, an exhalation port 618 through threaded cap 620, and a one-way valve 624 in a cylindrical portion 634. Adapter 616 is attachable and detachable to adapter 252 of endotracheal tube 216. Except as described herein, detection/resuscitator bag 604 may be of the type commonly used by clinicians. Different commercially available resuscitator bags have different types of one-way valves 624. It is believed that many, if not all, of these one-way valves would be acceptable for the present invention.

One embodiment of the present invention includes the following additional components to the standard detection/resuscitator bag 604. An evacuator bulb 630 may be inside or outside, on the top or bottom of ventilating bag 608. A connecting tube 632 connects the evacuator bulb 630 to an orifice 636 in the sidewall of adaptor 616. An indicator 640 is placed on connecting tube 632 or evacuator bulb 630 (or any where negative pressure is generated by evacuator bulb 630). A pressure valve 638 is positioned in cylindrical portion 634 between ventilating bag 608 and adapter 616.

Pressure valve 638 is designed such that oxygen can be easily squeezed through it into endotracheal tube 216 on compression of ventilating bag 608, but oxygen cannot be aspirated through valve 638 when a negative pressure is created by evacuator bulb 630 when tube tip 298 is occluded. If a significant amount of oxygen were to pass from ventilating bag 608 to tube 632, a significant negative pressure would not be created and indicator 640 would not be activated.

One structure for pressure valve 638 includes a spring and is illustrated in FIG. 28A. Under that embodiment, pressure valve 638 includes a spoke opening 666, a plate 670, and a spring 672. Cylindrical portion 634 is separated from bag 608 via spoke opening 666. Plate 670 is connected through spring 672 to the center of spoke opening 666. The diameter of plate 670 is greater than that of spoke opening 666, but less than that of cylindrical portion 634. Therefore, air flow created by squeezing bag 608 pushes plate 670 away from spoke opening 666. When bag 608 is released, plate 670 returns to spoke opening 666 under the force of spring 672. There is no force that causes it to opening again until bag 608 is again squeezed.

Of course, various other configurations could be used. Opening 666 does not have to be a spoke opening.

In a preferred embodiment, the threshold negative opening pressure of pressure valve 638 is greater negative pressure than the negative pressure required to activate indicator 640. For example, in the case where indicator 640 is an audible indicator such as in FIG. 14A, the pressure valve 638 (in the preferred embodiment) would have a higher threshold opening pressure than the "crack" pressure for indicator 640.

A venting on-off switch 646 is positioned within connecting tube 632. With venting switch 646 in the ON position (see FIGS. 29A and 29B), the evacuator bulb is connected via tube 632 to adapter 616 creating an "active" intubation detection system. By turning venting switch 646 to the OFF position (see FIGS. 30A and 30B), evacuator bulb 630 is vented into the atmosphere, resulting in deactivation of intubation detection system 600. Venting switch 646 helps avoid re-insufflation of low oxygen air back into the lungs. Once proper endotracheal tube location is confirmed, venting switch 646 will be turned to the OFF position to deactivate the detection system.

In operation, when intubation detector/resuscitator bag 604 is initially used on a just intubated patient, venting switch 646 will be in the ON position, as shown in FIGS. 29A and 29B. When venting switch 646 is in the ON position, air flows between bulb 630 and adapter 616. End adaptor 252 of endotracheal tube 216 is attached to adapter 616. Bag 608 and bulb 630 are simultaneously compressed through squeezing of the operator's hand. Oxygen is insufflated through barrel 634, out adapter 616 and into the patient via the endotracheal tube tip openings 302A and 302B (see FIG. 11).

Upon relaxation of the operator's hand, bag 608 and bulb 630 begin to spontaneously re-expand due to their preferred structural position in the expanded form. In typically operation, ventilating bag 608 re-expands by aspiration of 100% oxygen out of reservoir 610 (which in turn is refilled by oxygen source through tube 614). Bulb 630, however, cannot refill with oxygen from ventilating bag 608 or reservoir 610 due to pressure valve 638.

Bulb 630 therefore aspirates exhaled air from the patients lungs. If the endotracheal tube tip 298 is located within the patient's trachea, air is aspirated back through endotracheal tube 216 toward orifice 636, connecting tube 632, and bulb 630. The ability for bulb 630 to easily fill with air from the lungs prevents any generation of a "significant" negative pressure and no activation of indicator 640 occurs.

On the other hand, if endotracheal tube tip 298 is located within the esophagus, tube tip 298 becomes occluded as bulb 630 expands and no air is available for aspiration into bulb 630. This results in a "significant" negative pressure generation as bulb 630 attempts to re-expand, which causes activation of indicator 640. This signal warns the operator that the endotracheal tube is improperly located within the esophagus and should be removed and re-inserted properly.

Repeat squeezing of bag 608 and bulb 630 to ventilate the patient results in a similar sequence of events. Once the operator is convinced that the endotracheal tube tip 298 is properly located within the trachea, he or she deactivates the intubation detection system 600 by turning valve venting switch 646 to the OFF position, as shown in FIGS. 30A and 30B. As can be seen in FIGS. 30A and 30B, when venting switch 646 is in the OFF position, an orifice 652 becomes open allowing flow of air between bulb 630 and the outside. This results in air within bulb 630 being squeezed into and re-aspirated from the atmosphere. Deactivation of the detection system (through turning venting switch 646 to the OFF position) prevents continuous re-insufflation of exhaled air (low oxygen, high $CO_2$) back into the patient. The patients exhaled air will now leave via the exhalation port 618 (shown in FIGS. 28A and 28B).

D. Additional Information

The present invention is not limited to use with endotracheal tubes, but may be used with other tubular airway controlling devices such as an esophageal tracheal combitube or a pharyngeal tracheal lumen (PTL) airway.

The indicator may be placed over an orifice in the endotracheal tube (or other tubular airway controlling device) rather than over an orifice in an adapter, syringe or connecting tube 632. That an indicator is "positioned over an orifice" does not mean that the indicator does not also extend into the orifice.

As used herein, the term "pneumatically connected" means that two elements are connected by air at essentially the same air pressure. For example, in FIG. 11, indicator 232 is pneumatically connected to syringe 220 and endotracheal tube 216. In FIGS. 16A and 16B, indicator 350 is pneumatically connected to a portion of syringe 338, adapter 356, and endotracheal tube 216 when plunger seal 278 passes orifice 344. In FIG. 28A, indicator 640 is pneumatically connected to bulb 630. Indicator 640 would still be pneumatically connected to bulb 630 if indicator 640 were positioned directly in bulb 630 rather than being positioned adjacent on tube 632.

As used herein, the term "connect" and related words are used in an operational sense, and are not necessarily limited to a direct connection. For example, referring to FIG. 3, tube 84 is connected to tube 90, but not directly. Unless the term, "pneumatically connected" or some related expression is used, the connection is not necessarily limited to a pneumatically connection.

An indicator may include both vented (such as in FIGS. 19A and 19B) and non-vented portions (such as disk 320 in FIG. 14A).

As presently contemplated, orifice 344 may be approximately 0.10" (0.00254 meters) in diameter and punched or drilled in the side of the syringe barrel. Adapter section 256B may have a 15 mm inside diameter. Endotracheal tube 216 may be of the type marketed by the Mallinckrodt company of Glens Falls, N.Y., under the catalog number 86353. A preferred syringe is relatively short, has a relatively large handle, and has a volume of at least 60 cc. However, other syringes or sources of negative pressure also would be acceptable.

Various other adapters or adaption systems may be used rather than the illustrated adapter. For example, the adaptor may comprise a single piece or several pieces. Connector tubing may be PVC tubing or shrink wrap tubing, which may be less expensive than PVC. The syringe barrel and adapter may be one molded component.

Although esophageal intubation detector 214 and endotracheal tube 216 are typically not connected until after initial intubation, they may be connected before initial intubation.

In the case where the indicator is an audible indicator, an amplifier could be used to produce sufficient sound.

As used herein, the statement that the endotracheal tube is in the esophagus or the trachea means that a portion of, not all of, the endotracheal tube is in the esophagus or the trachea. Also, if holes 302A and 302B are occluded, tip 298 is said to be occluded. Further, the statement that syringe 220 is connected to endotracheal tube 216 does not require that they be directly connected. Rather, they may be indirectly connected by means of an adapter, such as adapter 240.

The above-described audible indicators are merely intended to provide examples of indicators. It will be apparent to those skilled in the art that various other audible and/or visual indicators may be used.

The present invention may be embodied in specific forms other than those of the preceding description, which are to be considered only as illustrative and not restrictive. Accordingly, the scope of the invention is indicated by the following claims, including equivalents thereof, rather than by the specific embodiments described in the preceding description.

What is claimed is:

1. An intubation detection system, comprising:
    a tube;
    a pressure changing source, including a chamber connected to the tube, to selectively change pressure in the chamber and the tube;
    a transducer to provide an electrical signal indicative of pressure at the transducer, the transducer being connected to the chamber;
    analyzing circuitry to receive the electrical signal and to determine a pressure history of the transducer pressure; and
    indication circuitry to indicate information regarding the pressure history.

2. The system of claim 1, wherein the tube includes a tubular airway controlling device having a tip inserted in a patient's throat, and the indication circuitry includes first and second lights, and wherein
    if the pressure history includes a very rapid decrease in the transducer pressure, the indication circuitry lights the first light; and
    if the pressure history includes the transducer pressure being relatively constant over a certain time period, the indication circuitry lights the second light.

3. The system of claim 2, wherein the indication circuitry further includes a third light, and wherein if the pressure history includes a relatively slow decrease in the transducer pressure, the indication circuitry lights the third light.

4. The system of claim 1, wherein the tube includes a tubular airway controlling device having a tip inserted in a patient's throat, and the indication circuitry may assume first and second states, and wherein
    if the pressure history includes a very rapid decrease in the transducer pressure, the indication circuitry assumes the first state; and
    if the pressure history includes the transducer pressure being relatively constant over a certain time period, the indication circuitry assumes the second state.

5. The system of claim 4, wherein the indication circuitry may assume a third state, and wherein if the pressure history includes a relatively slow decrease in the transducer pressure, the indication circuitry assumes the third state.

6. The system of claim 5, wherein in the indication circuitry includes first, second, and third lights, and in the first, second, and third states, the indication circuitry lights the first, second, and third lights respectively.

7. The system of claim 1, wherein in the analyzing circuitry includes a port to provide signals indicative of the pressure history.

8. The system of claim 1, wherein the tube includes an adapter connectable to a tubular airway controlling device.

9. The system of claim 1, further comprising a flow restrictor, connected between the tube and the chamber, to restrict flow of air between the tube and the chamber.

10. The system of claim 9, wherein the flow restrictor restricts flow between the tube and the chamber such that immediately after activation of the pressure changing source, the pressure in the chamber is greater than the pressure in the tube.

11. The system of claim 1, further comprising an antechamber connected to the chamber.

12. The system of claim 11, wherein the transducer is directly connected to the antechamber.

13. The system of claim 1, wherein the pressure changing source includes a volume changing device.

14. The system of claim 1, wherein the pressure changing source includes a gas canister.

15. The system of claim 1, wherein the transducer is directly connected to the chamber.

16. The system of claim 1, wherein the transducer is inside the chamber.

17. The system of claim 1, further comprising an antechamber and wherein the transducer is connected to the chamber through the antechamber.

18. The system of claim 1, wherein the electrical signal is a first electrical signal and the transducer provides additional electrical signals received by the analyzing circuitry.

19. An intubation detection system, comprising:
    a tube;
    a pressure changing source, including a chamber connected to the tube, to selectively change pressure in the chamber and the tube;

a transducer to provide an electrical signal indicative of mass flow through the transducer, the transducer being connected to the chamber;

analyzing circuitry to receive the electrical signal and to determine a history of mass flow through the transducer; and indication circuitry to indicate information regarding the mass flow history.

20. The system of claim 19, wherein a differential between pressure at the chamber and pressure in the tube creates a mass flow.

21. The system of claim 19, wherein the tube includes a tubular airway controlling device including a tip, and wherein the amount of the mass flow history is indicative of wherein the tip is in a patient's esophagus or trachea.

22. The system of claim 19, wherein the tube includes a tubular airway controlling device including a tip, and wherein the amount of the mass flow history is indicative of whether the tip is in a patient's esophagus or trachea and certain other conditions.

23. An intubation detection system, comprising:

a tube including a tubular airway controlling device having a tip;

a pressure changing source, including a chamber connected to the tube, to selectively change pressure in the chamber and the tube;

a transducer to provide an electrical signal indicative of a pressure differential between pressure at the tip and the pressure in the chamber;

analyzing circuitry to receive the electrical signal and to determine a pressure differential history; and indication circuitry to indicate information regarding the pressure differential history.

24. The system of claim 23, wherein the tubular airway controlling device is an endotracheal tube.

25. The system of claim 23, further comprising a flow restrictor connected between the transducer and the tip.

26. A tubular connection system, comprising:

a first adapter including a female connector port;

a second adapter sized to be snugly inserted into and removed from the female connector port; and an O-ring positioned in the female connector port to create a back pressure and a resulting seal between the second adapter and the female connector port as the second adapter is inserted into the female connector port.

* * * * *

UNITED STATES PATENT AND TRADEMARK OFFICE
CERTIFICATE OF CORRECTION

PATENT NO. : 5,885,248
DATED : March 23, 1999
INVENTOR(S) : Denton

It is certified that error appears in the above-identified patent and that said Letters Patent is hereby corrected as shown below:

Title Page,

"Other Publications" on page 2,
Line 10, insert -- #M.R. Salem et al., "Use of the Self-Inflating Bulb for Detecting Esophageal Intubation After Esophageal Ventilation," Anesth Analg, 1993, 77:1227-31. --;
Line 18, change "Morbidlty" to -- Morbidly --;
Line 38, change "Icidence" to -- Incidence --.

Drawings,
In Fig. 21, change reference numeral "354" to -- 350 --.

Specification,

Column 6,
Line 2, change "levers" to --lever-- and after "and" insert -- grip --.

Column 7,
Line 47, after "raised" insert -- , --;

Column 8,
Line 4, change "device" to -- devices --;
Line 52, change "LED" to -- LEDs --.

Column 9,
Line 18, change "LED" to -- LEDs --;
Line 30, after "MALFUNCTION" insert -- . --;
Line 59, change "136" to -- 138 --;
Line 66, change "prevent" to -- prevents --.

Column 10,
Line 2, after "72" and before "." insert -- (see FIGS. 1A and 1B) --;
Line 28, change "shows a" to -- shows an --.

Column 11,
Line 29, change "58" to -- 258 --;

UNITED STATES PATENT AND TRADEMARK OFFICE
CERTIFICATE OF CORRECTION

PATENT NO. : 5,885,248
DATED : March 23, 1999
INVENTOR(S) : Denton

It is certified that error appears in the above-identified patent and that said Letters Patent is hereby corrected as shown below:

Column 12,
Line 6, after "and" insert -- orifice --;
Line 47, change "284" to -- 282 --;
Line 49, change "included" to -- includes --.

Column 13,
Line 6, after "lock" insert -- stem --.

Column 14,
Line 17, change "354" to -- 350 --;
Line 32, change "482" to -- 282 --;
Line 37, change "498" to -- 298 --;
Line 59, after "endotracheal" insert -- tube --.

Column 16,
Line 16, change "570" to --550-- and change "26)," to -- 25) are used, --;
Line 20, change "retraced." to -- retracted. --;
Line 21, change "480" to -- 490 --;
Line 23, change "provided, that" to -- provided that, --;
Line 62, change "detection/resuscitator" to -- intubation detection/resuscitator --.

Column 17,
Line 2, change "detection/resuscitator" to -- intubation detection/resuscitator --;
Line 14, change "any where" to -- anywhere --;
Line 37, change "opening" to -- open --.

Column 18,
Line 8, change "typically" to -- typical --;
Line 11, after "by" insert -- an --;
Line 14, after "630" insert -- , --; after "therefore" insert -- , --; and change "patients" to -- patient's --;
Line 42, change "patients" to -- patient's --.

Column 19,
Lines 6-7, change "pneumatically" to -- pneumatic --;
Line 15, change "company" to -- Company --;
Line 21, change "adaption" to -- adaptation --.

UNITED STATES PATENT AND TRADEMARK OFFICE
CERTIFICATE OF CORRECTION

PATENT NO.    : 5,885,248
DATED         : March 23, 1999
INVENTOR(S)   : Denton

It is certified that error appears in the above-identified patent and that said Letters Patent is hereby corrected as shown below:

Claims,

Claim 6, Column 20,
Line 29, after "wherein" delete "in";
Line 32, after "lights" insert -- , --.

Claim 7, Column 20,
Line 33, after "wherein" delete "in".

Claim 19, Column 21,
Line 5, after "of" insert -- the --.

Claim 20, Column 21,
Line 11, change "a" to -- the --; and

Claim 21, Column 21,
Line 15, change "wherein" to -- whether --.

Signed and Sealed this

Thirtieth Day of October, 2001

Attest:

NICHOLAS P. GODICI
Attesting Officer    Acting Director of the United States Patent and Trademark Office